United States Patent
Murata et al.

[11] Patent Number: 5,972,946
[45] Date of Patent: Oct. 26, 1999

[54] ACETAMIDE DERIVATIVE, PROCESS FOR PREPARING THE SAME, AND A PHARMACEUTICAL COMPOSITION CONTAINING THE SAME

[75] Inventors: Teruya Murata, Izumiotsu; Katsuhiko Hino, Nara-ken; Kiyoshi Furukawa, Shiga-ken; Makoto Oka, Ibaraki; Mari Itoh, Suita, all of Japan

[73] Assignee: Dainippon Pharmaceutical Co., Ltd., Osaka, Japan

[21] Appl. No.: 08/930,604

[22] PCT Filed: Apr. 10, 1996

[86] PCT No.: PCT/JP96/00977

§ 371 Date: Oct. 14, 1997

§ 102(e) Date: Oct. 14, 1997

[87] PCT Pub. No.: WO96/32383

PCT Pub. Date: Oct. 17, 1996

[30] Foreign Application Priority Data

Apr. 13, 1995 [JP] Japan .................................. 7-113937

[51] Int. Cl.[6] .................................................. A61K 31/505
[52] U.S. Cl. .......................... 514/256; 514/259; 514/247; 514/252; 548/311.1; 548/312.4; 548/316.4; 548/326.5
[58] Field of Search ...................... 514/256, 259, 514/247, 252; 548/311.1, 312.4, 316.4, 326.5

[56] References Cited

U.S. PATENT DOCUMENTS

| | | | |
|---|---|---|---|
| 3,631,036 | 12/1971 | Kim et al. ............................. | 260/247.2 |
| 3,631,045 | 12/1971 | Kim et al. ............................. | 260/256.5 |
| 4,499,094 | 2/1985 | Dubroeucq ............................. | 514/301 |
| 4,788,199 | 11/1988 | Benavides et al. ...................... | 514/259 |
| 5,026,711 | 6/1991 | Mendes et al. ......................... | 514/300 |

FOREIGN PATENT DOCUMENTS 07165721  6/1995  Japan .

OTHER PUBLICATIONS

Romeo et al., "2–Aryl–3–Indoleacetamides(FGIN–1): A New Class of Potent and Specific Ligands for the Mitochondrial DBI Receptor (MDR)" *J.Pharmacol.Exp. Ther.* 262:971–978 (1992).

derivatives *Pharmazie* 43:537–537 (1988).

*Primary Examiner*—James H. Reamer
*Attorney, Agent, or Firm*—Foley & Lardner

[57] ABSTRACT

An acetamide derivative of the formula (I):

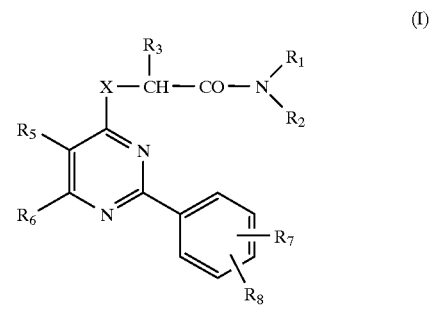

wherein X is —O— or —$NR_4$—, $R_1$ is H, lower alkyl, lower alkenyl or cycloalkyl-lower-alkyl, $R_2$ is lower alkyl, cycloalkyl, substituted or unsubstituted phenyl, etc., $R_3$ is H, lower alkyl or hydroxy-lower alkyl, $R_4$ is H, lower alkyl, etc., $R_5$ is H, lower alkyl, lower alkenyl, hydroxy-lower alkyl, etc., $R_6$ is H, lower alkyl, $CF_3$, substituted or unsubstituted phenyl, or $R_5$ and $R_6$ may optionally combine to form —$(CH_2)n$—, $R_7$ is H, halogen, lower alkyl, lower alkoxy, $CF_3$, OH, $NH_2$, etc., $R_8$ is H, halogen, lower alkyl or lower alkoxy, or a pharmaceutically acceptable acid addition salt thereof. The compounds of the present invention selectively act on the peripheral-type $BZ\omega_3$-receptor, and show excellent pharmacological activities, and hence, they are useful in the prophylaxis or treatment of central nervous disorders such as anxiety-related diseases, depression, epilepsy, etc.

19 Claims, No Drawings

ACETAMIDE DERIVATIVE, PROCESS FOR PREPARING THE SAME, AND A PHARMACEUTICAL COMPOSITION CONTAINING THE SAME

TECHNICAL FIELD

The present invention relates to a novel acetamide derivative selectively acting on the peripheral-type benzodiazepine receptors, more particularly, an acetamide derivative having 2-phenyl-4-pyrimidinylamino moiety or 2-phenyl-4-pyrimidinyloxy moiety, a process for preparing the same, and a pharmaceutical composition containing the same.

BACKGROUND ART

In the central nervous system of the mammals, including human, there are three kinds of benzodiazepine (hereinafter, occasionally referred to as BZ) recognition sites, and each is named as central-type ($\omega_1$, $\omega_2$) benzodiazepine receptors and a peripheral-type ($\omega_3$) benzodiazepine receptor, respectively (hereinafter, occasionally referred to as BZ$\omega_1$-receptor, BZ$\omega_2$-receptor and BZ$\omega_3$-receptor, respectively). Among them, the peripheral-type BZ-receptor unevenly distributes in the peripheral tissues or organs such as kidney, liver, heart, etc., but it especially distributes with high density in the cells of the endocrinium organs such as adrenal glands, testicles, etc., or in the cells deeply participating in the inflammation-immune system in whole body such as mast cells, lymphocytes, macrophages, blood platelets, etc., so that the physiological roles of the peripheral-type BZ-receptor have recently been drawing attention.

On the other hand, the peripheral-type BZ-receptor is present a lot in the mitochondrial membrane of glial cells in the brain, and it participates in cholesterol influx into the mitochondrial membrane, and hence, it is thought to act on the biosynthesis pathway of cholesterol into neurosteroids such as allopregnanolone, allotetrahydrodeoxycorticosterone (THDOC), etc. via pregnenolone. Thus, it is considered that stimulation of the peripheral-type BZ-receptor accelerates the synthesis of neurosteroids in the brain which affect the choride ion channel gating process by binding to the neurosteroid-specific recognition site on the γ-aminobutyric acid-A-receptor (hereinafter, occasionally referred to as GABA$_A$-receptor) [cf. Romeo, E., et al., J. Pharmacol. Exp. Ther., 262, 971–978 (1992)].

A compound having a non-BZ nucleus and selectively showing an affinity for the peripheral-type BZ-receptor has been disclosed in Japanese Patent First Publication (Kokai) No. 201756/1983 (EP-A-94271), and since then, various compounds are disclosed in many literatures including patent applications. However, there is no compound which has actually been used as a medicament.

As a compound having a non-BZ nucleus and selectively showing an affinity for the peripheral-type BZ-receptors, in addition to the above, there have been known the compounds disclosed in Japanese Patent First Publication (Kokai) Nos. 5946/1987 and 32058/1990.

Japanese Patent First Publication (Kokai) No. 5946/1987 (EP-A-205375, U.S. Pat. No. 4,788,199) discloses amide compounds of the following formula, which are bound to the peripheral-type BZ-receptor, and are useful as anxiolytics, anticonvulsants and antiangina agents, and for the treatment of immuno-deficiency syndrome.

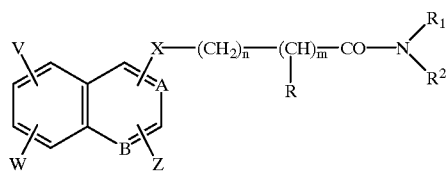

wherein A is a nitrogen atom or =CH—; B is a nitrogen atom or =CH—; V and W are the same or different and each a hydrogen atom, a halogen atom, an alkyl group or an alkoxy group both having 1 to 3 carbon atom, etc.; Z is bound in the ortho- or para-position with respect to the B, and is a phenyl group, a thienyl group, a pyridyl group, or a phenyl group substituted by 1 to 2 groups selected from a halogen atom, an alkyl group or an alkoxy group both having 1 to 4 carbon atoms, trifluoromethyl group and a nitro group; a chain of —X—(CH$_2$)$_n$—(CHR)$_m$—CONR$_1$R$_2$ is bound in the ortho- or para-position with respect to the B; R is a hydrogen atom or an alkyl group having 1 to 3 carbon atoms; R$_1$ and R$_2$ are the same or different and each a straight chain or branched chain alkyl group having 1 to 6 carbon atoms, a cycloalkyl group having 3 to 6 carbon atoms, a phenyl group, a phenylalkyl group or a cycloalkylalkyl group wherein the alkyl moiety has 1 to 3 carbon atoms and the cycloalkyl moiety has 3 to 6 carbon atoms, or an alkenyl group having 3 to 6 carbon atoms wherein the double bond is not located at the 1,2-position with respect to the nitrogen atom, and R$_1$ and R$_2$ may combine together with the nitrogen atom to which they are attached to form pyrrolidine, piperidine, morpholine or thiomorpholine ring; X is —CHR$_3$—, —NR$_4$—, —SO—, —SO$_2$—, an oxygen atom or a sulfur atom; R$_3$ is a hydrogen atom or an alkyl group having 1 to 3 carbon atoms; R$_4$ is an alkyl group having 1 to 3 carbon atoms; m is 0 or 1; and is 0, 1 or 2, provided that when X is —SO—, —SO$_2$— or —NR$_4$—, the total number of m+n should be at least 1, and that when both of A and B are a nitrogen atom and Z is at the para-position with respect to the B, X should not be —CHR$_3$—, and that when A is =CH—, B is a nitrogen atom, Z is in the ortho-position with respect to the B, X is an oxygen atom and R is a hydrogen atom, the total number of m+n is other than 1, and excluding 2-phenyl-4-quinolyl-N,N-dimethylcarbamate.

Japanese Patent First Publication (Kokai) No. 32058/1990 (EP-A-346208, U.S. Pat. No. 5026711) discloses that 4-amino-3-carboxyquinoline compounds of the following formula show an affinity for the peripheral-type BZ-receptor both in vivo and in vitro, and can be used in the prophylaxis or treatment of human cardiovascular diseases, or as an antiallergic agent, or in the prophylaxis or treatment of infectious diseases, or in the treatment of anxiety.

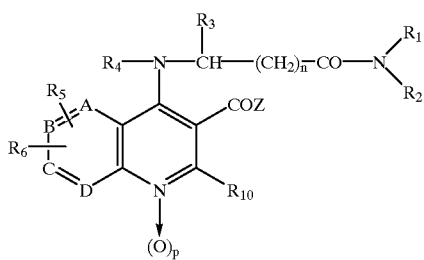

wherein R$_1$ and R$_2$ are each a hydrogen atom, a C$_1$–C$_6$ alkyl group, or a C$_2$–C$_6$ alkenyl group, a phenyl group or a benzyl group, or $R_1$ and $R_2$ may combine together with the nitrogen atom to which they are attached to form a $C_4$–$C_8$ saturated heterocyclic group; $R_3$ is a hydrogen atom, a $C_1$–$C_6$ alkyl group, a phenyl group or a $C_7$–$C_9$ phenylalkyl group; $R_4$ is a hydrogen atom or a $C_1$–$C_4$ alkyl group; $R_5$ and $R_6$ are each a hydrogen atom, a halogen atom, a $C_1$–$C_3$ alkyl or alkoxy group, a nitro group, or a trifluoromethyl group, or combine together to form a methylenedioxy group; Z is $OR_7$ ($R_7$ is a hydrogen atom or a $C_1$–$C_6$ alkyl group), $NR_8R_9$ ($R_8$ and $R_9$ are each a hydrogen atom, a $C_1$–$C_4$ alkyl group, a phenyl group or a benzyl group), a $C_1$–$C_4$ alkyl group, a benzyl group, a $C_4$–$C_6$ aryl group which may optionally have a heteroatom; $R_{10}$ is a hydrogen atom, a $C_1$–$C_4$ alkyl group or a phenyl group (provided that when Z is not a benzyl group or an aryl group, $R_3$ is not a hydrogen atom, and a phenyl group and a benzyl group may optionally be substituted by a halogen atom, a $C_1$–$C_3$ alkoxy, alkyl or thioalkyl group, a nitro group, a trifluoromethyl group or a hydroxy group, and these alkyl and alkoxy groups are straight chain, branched chain or cyclic ones, respectively); n is 0, 1 or 2; p is 0 or 1; one of A, B, C and D is N, and the other ones are each CH, or all A, B, C and D are each CH.

On the other hand, there are known some acetamide derivatives having a 2-phenyl-4-pyrimidinylamino moiety. For example, U.S. Pat. No. 3,631,036 discloses some compounds represented by 2-(5-cyano-2-phenyl-4-pyrimidinyl-amino) acetamide as a synthetic intermediate for 5-amino-2,6-di-substituted-7H-pyrrolo[2,3-d]pyrimidines. U.S. Pat. No. 3,631,045 discloses some compounds represented by 2-(5-cyano-6-methylamino-2-phenyl-4-pyrimidinylamino)-acetamide as a synthetic intermediate for 4,5-diamino-7H-pyrrolo[2,3-d]-pyrimidines. However, the pharmacological activities of these compounds have never been disclosed yet.

Besides, Pharmazie, 43, 537–538 (1988) discloses some compounds represented by 2-(5-acetyl-6-methyl-2-phenyl-4-pyrimidinylthio)-N-(4-chloro-phenyl) acetamide and 2-(5-acetyl-6-methyl-2-phenyl-4-pyrimidinylthio)-N-(4-methylphenyl) acetamide, as a synthetic intermediate for thieno[2,3-d]pyrimidine derivatives. Moreover, it is also disclosed in said literature that 2-(5-acetyl-6-methyl-2-phenyl-4-pyrimidinylthio)-N-(4-chlorophenyl)acetamide shows antibacterial activity against *Bacillus subtilis*.

DISCLOSURE OF INVENTION

The present inventors have intensively studied in order to prepare a compound acting selectively and potently on $BZ\omega_3$-receptor, and have found the acetamide derivatives of the following formula (I), and finally have accomplished the present invention.

An object of the present invention is to provide a novel acetamide derivative acting selectively and potently on $BZ\omega_3$-receptor, more particularly, to provide an acetamide derivative having a 2-phenyl-4-pyrimidinylamino moiety or a 2-phenyl-4-pyrimidinyloxy moiety. Especially, the present invention provides a useful compound having an anxiolytic activity and being useful in the treatment of immune diseases. Another object of the present invention is to provide a process for preparing said compound. Still further object of the present invention is to provide a pharmaceutical composition containing said compound. These objects and the advantageous features of the present invention are obvious to any skilled person in this art from the following description.

The present invention provides an acetamide derivative of the following formula (I), a pharmaceutically acceptable acid addition salt thereof (hereinafter, occasionally referred to as "the compound of the present invention"), a process for preparing the same, and a pharmaceutical composition containing the same.

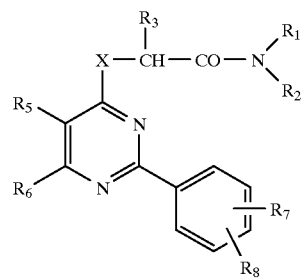

wherein X is —O— or —NR$_4$—, $R_1$ is a hydrogen atom, a lower alkyl group, a lower alkenyl group or a cyclolalkyl-lower alkyl group, $R_2$ is a lower alkyl group, a cycloalkyl group, a substituted or unsubstituted phenyl group, or a substituted or unsubstituted phenyl-lower alkyl group, or $R_1$ and $R_2$ may optionally combine together with the nitrogen atom to which they are attached to form a group of the formula:

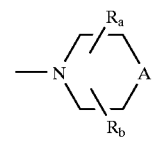

wherein A is a single bond, —CH$_2$—, —O— or —NH—, $R_a$ and $R_b$ are the same or different and each a hydrogen atom or a lower alkyl group, or when A is a single bond, and $R_a$ and $R_b$ are located at the 2-position and the 3-position, respectively, the carbon atoms of the 2-position and the 3-position and $R_a$ and $R_b$ may optionally combine to form a phenyl ring, $R_3$ is a hydrogen atom, a lower alkyl group or a hydroxy-lower alkyl group, $R_4$ is a hydrogen atom or a lower alkyl group, or $R_3$ and $R_4$ may optionally combine together with the carbon atom and the nitrogen atom to which they are attached to form pyrrolidine, piperidine, or 2,3-dihydro-1H-indole ring, $R_5$ is a hydrogen atom, a lower alkyl group, a lower alkenyl group, a hydroxy-lower alkyl group, a substituted or unsubstituted benzyloxy-lower alkyl group, an acyloxy-lower alkyl group, a lower alkoxy-lower alkyl group, a trifluoromethyl group, a halogen atom, an amino group, a mono- or di-lower alkylamino group, an acylamino group, an amino-lower alkyl group, a nitro group, a carbamoyl group, a mono- or di-lower alkyl-carbamoyl group, a carboxyl group, a protected carboxyl group, a carboxy-lower alkyl group or a protected carboxy-lower alkyl group, $R_6$ is a hydrogen atom, a lower alkyl group, a trifluoromethyl group or a substituted or unsubstituted phenyl group, or $R_5$ and $R_6$ may optionally combine to form —(CH$_2$)$_n$— (n is 3, 4, 5 or 6), $R_7$ is a hydrogen atom, a halogen atom, a lower alkyl group, a lower alkoxy group, a trifluoromethyl group, a hydroxy group, an amino group, a mono- or di-lower alkylamino group, a cyano group or a nitro group, $R_8$ is a hydrogen atom, a halogen atom, a lower alkyl group or a lower alkoxy group.

The pharmaceutically acceptable acid addition salt of the compound of the formula (I) includes a pharmaceutically acceptable acid addition salt of the compound of the formula (I) which shows basicity enough to form an acid addition salt thereof, for example, a salt with an inorganic acid such as hydrochloride, hydrobromide, hydroiodide, sulfate, phosphate, etc., or a salt with an organic acid such as maleate, fumarate, oxalate, citrate, tartrate, lactate, benzoate, methanesulfonate, etc. The compound of the formula (I) and an acid addition salt thereof may exist in the form of a hydrate and/or a solvate, and the present invention also includes these hydrates and solvates as well.

The compound of the formula (I) may have one or more asymmetric carbon atoms, and by which stereoisomers thereof are possible, and the compound of the formula (I) may exist in a mixture of two or more stereoisomers. The present invention also includes these stereoisomers, a mixture thereof, and a racemic mixture thereof.

The terms used in the present description and claims are explained below.

The lower alkyl group and the lower alkoxy group include a straight chain or branched chain alkyl or alkoxy group having 1 to 6 carbon atoms, respectively, unless defined otherwise. The lower alkyl group is, for example, methyl, ethyl, propyl, isopropyl, butyl, isobutyl, pentyl, and hexyl. The lower alkyl groups for $R_3$, $R_4$, $R_5$, $R_6$, $R_7$ and $R_8$ are preferably ones having 1 to 4 carbon atoms. The lower alkoxy group is, for example, methoxy, ethoxy, propoxy, and butoxy. The lower alkenyl group includes ones having a double bond except for between the 1- and 2-positions, and having 3 to 6 carbon atoms, for example, allyl, and 2-butenyl. The cycloalkyl group includes ones having 3 to 8 carbon atoms, for example, cyclopropyl, cyclobutyl, cyclopentyl, cyclohexyl, cycloheptyl, and cyclooctyl. The cycloalkyl-lower alkyl group includes an alkyl group having 1 to 4 carbon atoms which is substituted by one of the above mentioned cycloalkyl groups, for example, cyclopropylmethyl, cyclopentylmethyl, and cyclohexylmethyl. The halogen atom is fluorine, chlorine, bromine, and iodine.

The substituted or unsubstituted phenyl group includes a phenyl group which may optionally be substituted by one or two groups selected from a halogen atom, a $C_1$–$C_3$ alkyl group, a $C_1$–$C_3$ alkoxy group, a trifluoromethyl group, an amino group, a mono- or di-$C_1$–$C_3$ alkylamino group, a cyano group and a nitro group, for example, phenyl; 2-, 3- or 4-chlorophenyl; 2-, 3- or 4-bromophenyl; 2-, 3- or 4-fluorophenyl; 2,4-dichlorophenyl; 2,4-dibromophenyl; 2,4-difluorophenyl; 2-, 3- or 4-methylphenyl, 2-, 3- or 4-methoxyphenyl, 2-, 3- or 4-trifluoromethylphenyl; 2-, 3- or 4-aminophenyl; 2-, 3- or 4-methylaminophenyl; 2-, 3- or 4-dimethylaminophenyl; 2-, 3- or 4-cyanophenyl; and 2-, 3- or 4-nitrophenyl.

The examples of a group of the formula:

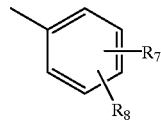

includes ones being exemplified above for the substituted or unsubstituted phenyl group, and more preferable ones are phenyl, 4- or 3-chlorophenyl, 4- or 3-bromophenyl, 4-or 3-fluorophenyl, and 4-methoxyphenyl. The substituted or unsubstituted phenyl-lower alkyl group includes an alkyl group having 1 to 4 carbon atoms which is substituted by one of the above mentioned substituted or unsubstituted phenyl groups, for example, benzyl, 2-, 3- or 4-chlorobenzyl, 4-bromobenzyl, 3- or 4-fluorobenzyl, 4-methylbenzyl, 4-methoxybenzyl, phenethyl, and 2-(4-chlorophenyl)ethyl.

The hydroxy-lower alkyl group includes an alkyl group having 1 to 4 carbon atoms which is substituted by a hydroxy group, for example, hydroxy-methyl, 2-hydroxyethyl, and 3-hydroxypropyl. The substituted or unsubstituted benzyloxy-lower alkyl group includes a lower alkyl group substituted by one or two groups selected from a benzyloxy group wherein the phenyl moiety may optionally be substituted by a halogen atom, a $C_1$–$C_3$ alkyl group and a $C_1$–$C_3$ alkoxy group, for example, benzyloxymethyl, 2-, 3- or 4-chlorobenzyloxymethyl, 3-bromobenzyloxymethyl, 4-fluorobenzyloxymethyl, 2,4- or 3,4-dichlorobenzyloxymethyl, 4-methylbenzyloxymethyl, 2-, 3- or 4-methoxybenzyloxymethyl, and 2-benzyloxyethyl. The acyl group includes an alkanoyl group having 2 to 4 carbon atom or a benzoyl group which may optionally be substituted by a halogen atom, a $C_1$–$C_3$ alkyl group or a $C_1$–$C_3$ alkoxy group, for example, acetyl, propionyl, benzoyl, 2-, 3- or 4-chlorobenzoyl, 2-, 3- or 4-bromobenzoyl, 2-, 3- or 4-fluorobenzoyl, 4-methylbenzoyl, and 4-methoxybenzoyl. The acyloxy-lower alkyl group includes a lower alkyl group substituted by an acyloxy group which is introduced from the above mentioned acyl groups, for example, acetoxymethyl, benzoyloxymethyl, 4-chlorobenzoyloxymethyl, 3-bromobenzoyloxymethyl, 4-fluorobenzoyloxymethyl, 2-methyl-benzoyloxymethyl, and 4-methoxybenzoyloxymethyl. The lower alkoxy-lower alkyl group includes an alkyl group having 1 to 4 carbon atoms which is substituted by an alkoxy group having 1 to 4 carbon atoms, for example, methoxymethyl, ethoxymethyl, 2-methoxyethyl, and 3-methoxypropyl.

The mono- or di-lower alkylamino group includes an amino group substituted by one or two alkyl groups having 1 to 4 carbon atoms, for example, methylamino, ethylamino, propylamino, dimethylamino, diethylamino, dipropylamino, and ethylmethylamino. The acylamino group includes an amino group substituted by the above mentioned acyl group, for example, acetylamino, propionylamino, benzoylamino, 4-chlorobenzoylamino, and 4-fluorobenzoylamino. The amino-lower alkyl group includes an alkyl group having 1 to 4 carbon atoms which is substituted by an amino group, for example, aminomethyl, 2-aminoethyl, and $^3$-aminopropyl. The mono- or di-lower alkyl-carbamoyl group includes a carbamoyl group substituted by one or two alkyl groups having 1 to 4 carbon atoms, for example, methylcarbamoyl, dimethylcarbamoyl, diethylcarbamoyl, and dipropylcarbamoyl. The protected carboxyl group includes a carboxyl group which is protected by a protecting group which can easily be removed by hydrolysis or hydrogenolysis, for example, a carboxyl group protected by a $C_1$–$C_4$ alkyl group or by a benzyl group which may optionally be substituted by one or two groups selected from a halogen atom, a $C_1$–$C_3$ alkyl group and a $C_1$–$C_3$ alkoxy group. The examples of the protected carboxyl group are methoxycarbonyl, ethoxycarbonyl, propoxycarbonyl, butoxycarbonyl, benzyloxycarbonyl, 4-chlorobenzyloxycarbonyl, 4-fluorobenzyloxycarbonyl, 4-methylbenzyloxycarbonyl, and 4-methoxybenzyloxycarbonyl. Among them, methoxycarbonyl, ethoxycarbonyl and benzyloxycarbonyl are preferable. The protected carboxy-lower alkyl group includes an alkyl group having 1 to 4 carbon atoms which is substituted by the above mentioned protected carboxyl group, for example, methoxy-carbonylmethyl, ethoxycarbonylmethyl, benzyloxycarbonylmethyl, and 2-ethoxycarbonylethyl.

Among the compounds of the present invention, the preferable one is a compound of the formula (I) wherein $R_1$ and $R_2$ are the same or different and each a lower alkyl group, or $R_1$ is a lower alkyl group, a lower alkenyl group or a cycloalkyl-lower alkyl group, $R_2$ is a substituted or unsubstituted phenyl group, or $R_1$ and $R_2$ may combine together with the nitrogen atom to which they are attached to form a group of the formula:

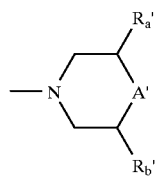

(wherein A' is —$CH_2$— or —O—, $R_a'$ and $R_b'$ are the same or different and each a lower alkyl group), $R_5$ is a hydrogen atom, a lower alkyl group, a hydroxy-lower alkyl group, a halogen atom, an amino group, an acylamino group, a nitro group or a protected carboxyl group, and X, $R_3$, $R_6$, $R_7$ and $R_8$ are the same as defined above, or a pharmaceutically acceptable acid addition salt thereof.

The more preferable compound of the present invention is a compound of the formula (I) wherein $R_1$ and $R_2$ are the same or different and each methyl group, ethyl group, propyl group, isopropyl group or butyl group, or $R_1$ is methyl group, ethyl group, propyl group, isopropyl group, butyl group, allyl group or cyclopropylmethyl group, $R_2$ is phenyl group, or a phenyl group substituted by a halogen atom or methoxy group, $R_3$ is a hydrogen atom, $R_5$ is a hydrogen atom, methyl group, ethyl group or hydroxymethyl group, $R_6$ is methyl group or phenyl group, or $R_5$ and $R_6$ may optionally combine to form —$(CH_2)_4$—, $R_7$ is a hydrogen atom, a halogen atom, a $C_1$-$C_3$ alkoxy group, trifluoromethyl group, amino group or nitro group, $R_8$ is a hydrogen atom, and X and $R_4$ are the same as defined above, or a pharmaceutically acceptable acid addition salt thereof.

The further preferable compound of the present invention is a compound of the formula (I) wherein X is —O— or —$NR_4'$—, $R_1$ and $R_2$ are the same or different and each ethyl group, propyl group or butyl group, or $R_1$ is methyl group, ethyl group, propyl group, allyl group or cyclopropylmethyl group, and $R_2$ is phenyl group, a halogenophenyl group or a methoxyphenyl group, $R_3$ is a hydrogen atom, $R_4'$ is a hydrogen atom, methyl group or ethyl group, or $R_3$ and $R_4'$ may optionally combine together with the carbon atom and the nitrogen atom to which they are attached to form pyrrolidine ring or 2,3-dihydro-1H-indole ring, $R_7$ is a hydrogen atom, a halogen atom, methoxy group, trifluoromethyl group, amino group or nitro group, $R_8$ is a hydrogen atom, $R_5$ and $R_6$ are the same as defined just in the above, or a pharmaceutically acceptable acid addition salt thereof.

The especially preferable compound of the present invention is an acetamide derivative of the following formula (I') or the formula (I"), or a pharmaceutically acceptable acid addition salt thereof.

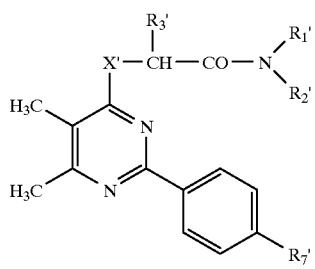

wherein X' is —O— or —$NR_4''$—, $R_1'$ and $R_2'$ are both ethyl group or propyl group, or $R_1'$ is methyl group, ethyl group, propyl group, allyl group or cyclopropylmethyl group, and $R_2'$ is phenyl group, 4-halogenophenyl group, or 4-methoxyphenyl group, $R_3'$ is a hydrogen atom, $R^{4''}$ is a hydrogen atom, methyl group or ethyl group, $R_7'$ is a hydrogen atom, a halogen atom, methoxy group, a trifluoromethyl group, an amino group or a nitro group. Further, among the compounds of the formula (I'), the compounds of the formula (I') wherein X' is —O— or X' is —NH— are most preferable.

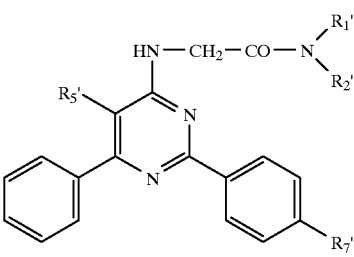

wherein $R_5'$ is a hydrogen atom, methyl group or ethyl group, and $R_1'$, $R_2'$ and $R_7'$ are the same as defined above.

The examples of the most preferable compound of the present invention are the following compounds and pharmaceutically acceptable acid addition salts thereof.

2-[2-(4-Chlorophenyl)-5,6-dimethyl-4-pyrimidinylamino]-N,N-dipropylacetamide;

2-[2-(4-Chlorophenyl)-5,6-dimethyl-4-pyrimidinylamino]-N,N-diethylacetamide;

2-[2-(4-Chlorophenyl)-5,6-dimethyl-4-pyrimidinylamino]-N-methyl-N-phenylacetamide;

N-(4-Chlorophenyl)-N-methyl-2-(5,6-dimethyl-2-phenyl-4-pyrimidinylamino)acetamide;

2-[2-(4-Chlorophenyl)-5,6-dimethyl-4-pyrimidinylamino]-N-(4-fluorophenyl)-N-methylacetamide;

2-[2-(4-Chlorophenyl)-5,6-dimethyl-4-pyrimidinylamino]-N-(4-methoxyphenyl)-N-methylacetamide;

2-(5,6-Dimethyl-2-phenyl-4-pyrimidinylamino)-N-phenyl-N-propylacetamide;

2-[2-(4-Chlorophenyl)-5,6-dimethyl-4-pyrimidinylamino]-N-ethyl-N-phenylacetamide;

2-(5,6-Dimethyl-2-phenyl-4-pyrimidinyloxy)-N,N-dipropylacetamide;

2-(2,6-Diphenyl-4-pyrimidinylamino)-N,N-dipropylacetamide;

2-[5,6-Dimethyl-2-(4-trifluoromethylphenyl)-4-pyrimidinylamino]-N,N-dipropylacetamide;

2-[2-(4-Aminophenyl)-5,6-dimethyl-4-pyrimidinyloxy]-N-ethyl-N-phenyl-acetamide;

N-(4-Chlorophenyl)-N-methyl-2-(5,6-dimethyl-2-phenyl-4-pyrimidinyloxy)acetamide; and 2-(5,6-Dimethyl-2-phenyl-4-pyrimidinyloxy)-N-phenyl-N-propylacetamide The representative compounds of the present invention are, in addition to the compounds of the following Examples, the compounds of the following Tables 1 to 4, and a pharmaceutically acceptable acid addition salt thereof.

In Tables 1 to 4, the following Reference Examples and Examples, the following abbreviations are used in order to simplify the disclosure.

Ac: Acetyl group

Me: Methyl group

Et: Ethyl group

Pr: Propyl group i-Pr: Isopropyl group

Bu: Butyl group i-Bu: Isobutyl group

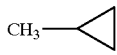 : Cyclopropylmethyl group

Ph: Phenyl group

Thus, for example, Ph-4-Cl means 4-chlorophenyl group, and Ph-4-F means 4-fluorophenyl group.

TABLE 1

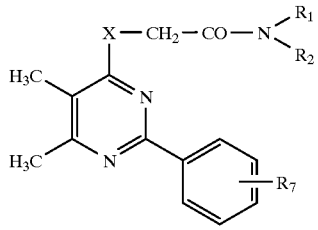

| $R_1$ | $R_2$ | $R_7$ | X |
|---|---|---|---|
| Me | Ph-2-F | H | NH |
| Me | Ph-2-Br | H | NH |
| i-Pr | i-Pr | 4-Cl | NH |
| Me | Ph-2-Cl | 4-Cl | NH |
| Me | Ph-3-F | 4-Cl | NH |
| Et | Ph-4-Cl | 4-Cl | NH |
| Et | Ph-4-F | 4-Cl | NH |
| Pr | Pr | 2-Br | NH |
| Pr | Pr | 4-Br | NH |
| Bu | Bu | 4-Br | NH |
| Me | Ph | 4-Br | NH |
| Me | Ph | 4-Br | NH |
| Et | Ph-4-Cl | 4-Br | NH |
| Pr | Pr | 3-F | NH |
| Me | Ph | 2-F | NH |
| Me | Ph-2-Cl | 4-F | NH |
| Me | Ph-3-Cl | 4-F | NH |
| Me | Ph-2-F | 4-F | NH |
| Et | Ph-4-F | 4-F | NH |
| Bu | Bu | 4-OMe | NH |
| Me | Ph-3-F | 4-OMe | NH |
| Et | Ph-4-F | 4-OMe | NH |
| Pr | Pr | 4-OH | NH |
| Me | Ph | 4-NH$_2$ | NH |
| Bu | Bu | H | NMe |
| Me | Ph-4-Cl | 4-F | NMe |
| Me | Ph-4-F | 4-Cl | NMe |

TABLE 1-continued

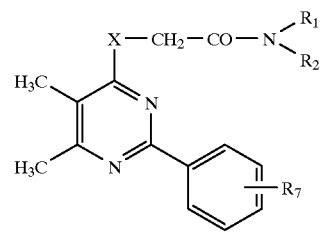

| $R_1$ | $R_2$ | $R_7$ | X |
|---|---|---|---|
| Pr | Pr | H | NEt |
| Pr | Pr | 4-F | NEt |
| Me | Ph | 4-Cl | NPr |
| Pr | Pr | 4-NH$_2$ | O |
| i-Pr | i-Pr | 4-Cl | O |
| Bu | Bu | 4-Cl | O |
| Me | Ph | 4-NH$_2$ | O |
| Me | Ph-4-Cl | 3-F | O |
| Me | Ph-2-F | 4-Cl | O |
| Et | Ph-4-Cl | H | O |
| Et | Ph-4-Cl | 4-F | O |
| Et | Ph-4-F | 4-Cl | O |

TABLE 2

| $R_1$ | $R_2$ | $R_5$ | $R_9$ | $R_7$ | X |
|---|---|---|---|---|---|
| Et | Et | H | H | 4-Cl | NH |
| Pr | Pr | H | H | 4-F | NH |
| Pr | Pr | H | H | 2-F | NH |
| i-Pr | i-Pr | H | H | H | NH |
| Bu | Bu | H | H | H | NH |
| Bu | Bu | H | H | 4-F | NH |
| Me | Ph | H | H | 4-F | NH |
| Me | Ph | H | H | 3-Cl | NH |
| Me | Ph-4-Cl | H | H | 4-Cl | NH |
| Me | Ph-2-Cl | H | H | 4-F | NH |
| Me | Ph-4-F | H | H | 4-Cl | NH |
| Me | Ph-2-F | H | H | 4-F | NH |
| Et | Ph | H | H | 4-Cl | NH |
| Et | Ph-4-Cl | H | H | H | NH |
| Pr | Pr | Me | H | 4-F | NH |
| i-Pr | i-Pr | Me | H | 4-Cl | NH |
| Bu | Bu | Me | H | 4-F | NH |
| Me | Ph | Me | H | 4-Cl | NH |
| Me | Ph-4-Cl | Me | H | H | NH |
| Me | Ph-4-Cl | Me | H | 4-F | NH |
| Me | Ph-4-F | Me | H | 4-Cl | NH |
| Et | Ph | Me | H | H | NH |
| Et | Ph | Me | H | 4-Cl | NH |
| Pr | Pr | H | 4-Cl | 4-F | NH |
| Bu | Bu | H | 4-NO$_2$ | 4-F | NH |
| Me | Ph-4-Cl | H | 2-Me | H | NH |
| Pr | Pr | Me | 4-Cl | 4-F | NH |
| Bu | Bu | Me | 4-NO$_2$ | 4-F | NH |
| Me | Ph-4-Cl | Me | 2-Me | H | NH |
| Et | Et | H | H | 3-Cl | O |
| Pr | Pr | H | H | 4-Cl | O |
| i-Pr | i-Pr | H | H | 4-F | O |
| Bu | Bu | H | H | 4-Cl | O |

TABLE 2-continued

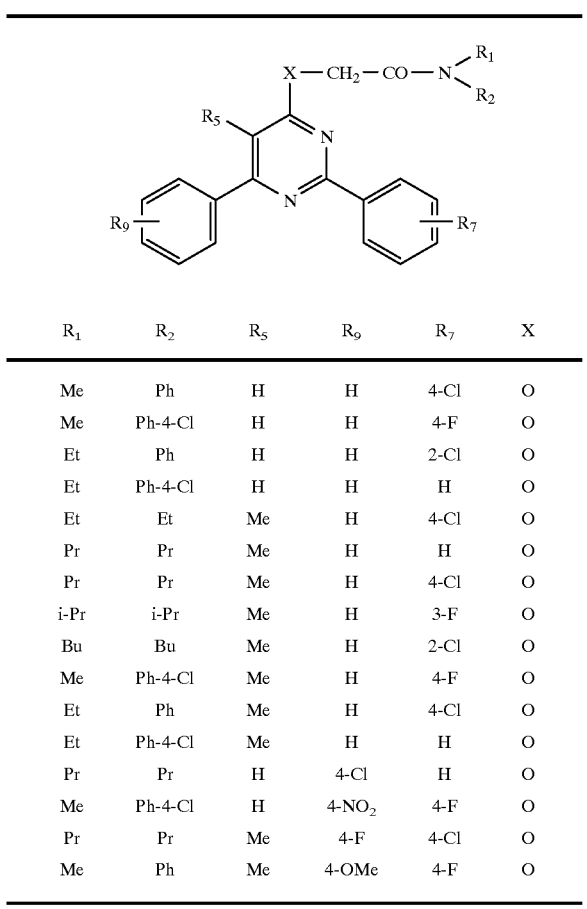

| $R_1$ | $R_2$ | $R_5$ | $R_9$ | $R_7$ | X |
|---|---|---|---|---|---|
| Me | Ph | H | H | 4-Cl | O |
| Me | Ph-4-Cl | H | H | 4-F | O |
| Et | Ph | H | H | 2-Cl | O |
| Et | Ph-4-Cl | H | H | H | O |
| Et | Et | Me | H | 4-Cl | O |
| Pr | Pr | Me | H | H | O |
| Pr | Pr | Me | H | 4-Cl | O |
| i-Pr | i-Pr | Me | H | 3-F | O |
| Bu | Bu | Me | H | 2-Cl | O |
| Me | Ph-4-Cl | Me | H | 4-F | O |
| Et | Ph | Me | H | 4-Cl | O |
| Et | Ph-4-Cl | Me | H | H | O |
| Pr | Pr | H | 4-Cl | H | O |
| Me | Ph-4-Cl | H | 4-NO$_2$ | 4-F | O |
| Pr | Pr | Me | 4-F | 4-Cl | O |
| Me | Ph | Me | 4-OMe | 4-F | O |

TABLE 3

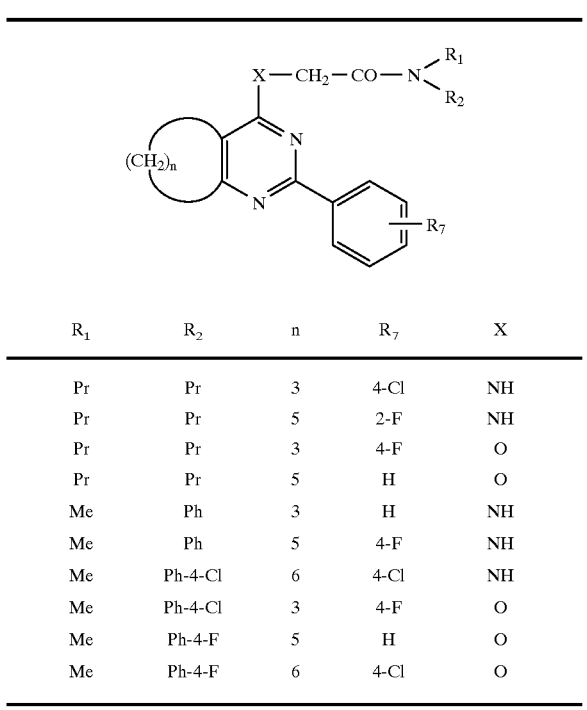

| $R_1$ | $R_2$ | n | $R_7$ | X |
|---|---|---|---|---|
| Pr | Pr | 3 | 4-Cl | NH |
| Pr | Pr | 5 | 2-F | NH |
| Pr | Pr | 3 | 4-F | O |
| Pr | Pr | 5 | H | O |
| Me | Ph | 3 | H | NH |
| Me | Ph | 5 | 4-F | NH |
| Me | Ph-4-Cl | 6 | 4-Cl | NH |
| Me | Ph-4-Cl | 3 | 4-F | O |
| Me | Ph-4-F | 5 | H | O |
| Me | Ph-4-F | 6 | 4-Cl | O |

TABLE 4

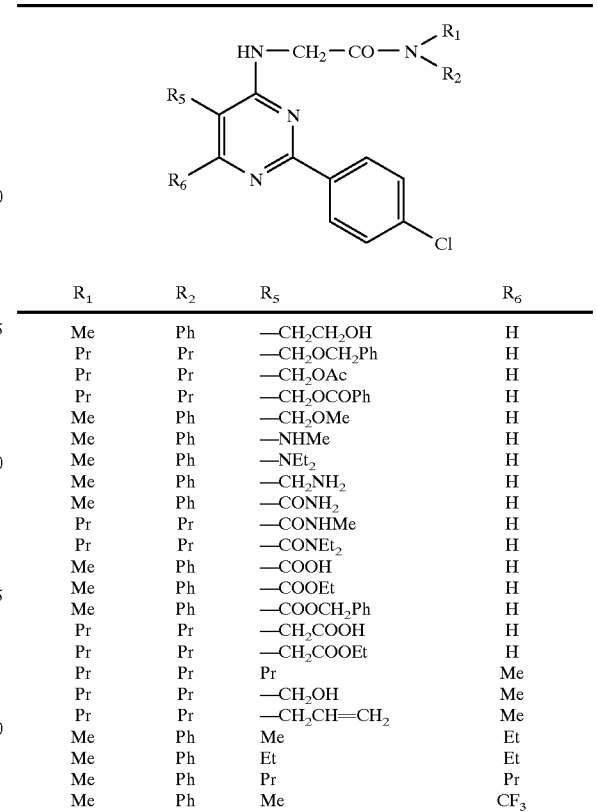

| $R_1$ | $R_2$ | $R_5$ | $R_6$ |
|---|---|---|---|
| Me | Ph | —CH$_2$CH$_2$OH | H |
| Pr | Pr | —CH$_2$OCH$_2$Ph | H |
| Pr | Pr | —CH$_2$OAc | H |
| Pr | Pr | —CH$_2$OCOPh | H |
| Me | Ph | —CH$_2$OMe | H |
| Me | Ph | —NHMe | H |
| Me | Ph | —NEt$_2$ | H |
| Me | Ph | —CH$_2$NH$_2$ | H |
| Me | Ph | —CONH$_2$ | H |
| Pr | Pr | —CONHMe | H |
| Pr | Pr | —CONEt$_2$ | H |
| Me | Ph | —COOH | H |
| Me | Ph | —COOEt | H |
| Me | Ph | —COOCH$_2$Ph | H |
| Pr | Pr | —CH$_2$COOH | H |
| Pr | Pr | —CH$_2$COOEt | H |
| Pr | Pr | Pr | Me |
| Pr | Pr | —CH$_2$OH | Me |
| Pr | Pr | —CH$_2$CH=CH$_2$ | Me |
| Me | Ph | Me | Et |
| Me | Ph | Et | Et |
| Me | Ph | Pr | Pr |
| Me | Ph | Me | CF$_3$ |

The compounds of the present invention may be prepared, for example, by the following processes.

Process (a)

The compound of the formula (I) wherein X is —NR$_4$— is prepared by reacting a compound of the formula (II):

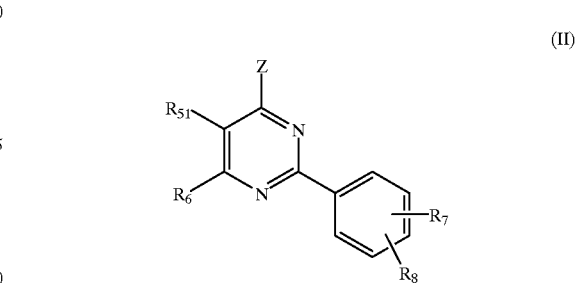

(II)

wherein Z is a leaving atom or a leaving group, $R_{51}$ is the same groups as defined above for $R_5$ except that a hydroxy-lower alkyl group, an amino group, an amino-lower alkyl group, a carboxyl group and a carboxy-lower alkyl group are protected ones, and $R_6$, $R_7$ and $R_8$ are the same as defined above, with a compound of the formula (III):

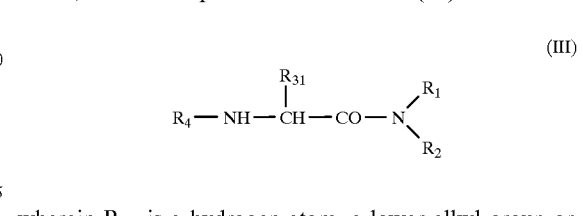

(III)

wherein $R_{31}$ is a hydrogen atom, a lower alkyl group or a protected hydroxy-lower alkyl group, and $R_1$, $R_2$ and $R_4$ are the same as defined above, if necessary, followed by removing the protecting groups from the product.

The leaving atom or the leaving group represented by Z in the above formula (II) includes an atom or a group which may be removed in the form of HZ together with the hydrogen atom of the NH moiety of the compound (III) under the reaction conditions, for example, a halogen atom (e.g. chlorine, bromine, iodine), a lower alkylsulfonyloxy group (e.g. methanesulfonyloxy), a trihalogenomethanesulfonyloxy group (e.g. trifluoromethanesulfonyloxy), and an arylsulfonyloxy group (e.g. benzenesulfonyloxy, p-toluenesulfonyloxy).

The protected hydroxy group for $R_{31}$ or $R_{51}$ in the above formulae (II) and (III) includes a hydroxy group being protected by a protecting group which may be removed by hydrogenolysis, for example, benzyloxy, 4-chlorobenzyloxy, 3-bromobenzyloxy, 4-fluorobenzyloxy, 4-methylbenzyloxy, and 4-methoxybenzyloxy. The protected amino group or protected amino moiety for $R_{51}$ in the formula (II) includes an amino group or amino moiety being protected by a protecting group which can be removed by hydrogenolysis, for example, benzyloxycarbonylamino, 3- or 4-chlorobenzyloxycarbonylamino, 4-bromobenzyloxycarbonylamino, 4-fluorobenzyloxycarbonylamino, 4-methylbenzyloxycarbonylamino, and 4-methoxybenzyloxycarbonylamino. The protected carboxyl group or protected carboxyl moiety for $R_{51}$ in the formula (II) includes a carboxyl group or carboxyl moiety being protected by a protecting group which can be removed by hydrolysis or hydrogenolysis, for example, ones which are exemplified above in the explanation of the terms used in the present disclosure and claims.

The reaction of the compound (II) and the compound (III) is carried out under atmospheric pressure or under pressure in a suitable solvent or without a solvent.

The solvent includes, for example, aromatic hydrocarbons (e.g. toluene, xylene), ketones (e.g. methyl ethyl ketone, methyl isobutyl ketone), ethers (e.g. dioxane, diglyme), alcohols (e.g. ethanol, isopropanol, butanol), acetonitrile, dimethylformamide, and dimethylsulfoxide. The reaction is preferably carried out in the presence of a base, and the base includes, for example, alkali metal carbonates (e.g. sodium carbonate, potassium carbonate), alkali metal hydrogen carbonates (e.g. sodium hydrogen carbonate, potassium hydrogen carbonate), and tertiary amines (e.g. triethylamine), but the excess amount of the compound (III) may be used instead of a base. The reaction temperature varies according to the kinds of the starting compounds or the reaction conditions, but it is usually in the range of about 40° C. to about 200° C., more preferably in the range of about 100° C. to about 170° C.

When $R_{31}$ and/or $R_{51}$ of the product thus obtained have a protecting group, these protecting groups may be removed by hydrogenolysis and/or hydrolysis.

The hydrogenolysis is carried out by a conventional method, for example, by reacting with hydrogen in a suitable solvent in the presence of a catalyst such as palladium-carbon, Raney-nickel, etc. The solvent includes, for example, alcohols (e.g. ethanol, methanol), water, acetic acid, dioxane and tetrahydrofuran. The reaction is usually carried out at a temperature of from about 0° C. to about 80° C., under atmospheric pressure or under pressure.

The hydrolysis is carried out by a conventional method, for example, by contacting with water in a suitable solvent under acidic or basic conditions. The solvent includes, for example, alcohols (e.g. methanol, ethanol, isopropanol), dioxane, water, and a mixture of these solvents. The acid includes, for example, mineral acids (e.g. hydrochloric acid, sulfuric acid), and organic acids (e.g. formic acid, acetic acid, propionic acid, oxalic acid). The base includes, for example, alkali metal hydroxides (e.g. sodium hydroxide, potassium hydroxide), and alkali metal carbonates (e.g. sodium carbonate, potassium carbonate). The reaction is usually carried out at a temperature of from about 20° C. to 100° C.

The starting compound (II) is prepared by subjecting a compound of the formula (IV):

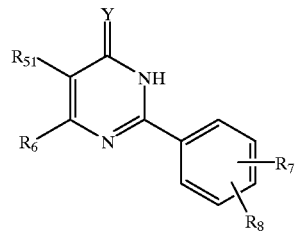

(IV)

wherein Y is an oxygen atom or a sulfur atom, and $R_{51}$, $R_6$, $R_7$ and $R_8$ are the same as defined above, to halogenation or sulfonylation by a conventional method.

The halogenation is carried out by reacting the compound (IV) with a halogenating agent (e.g. phosphorus oxychloride, phosphorus tribromide). The sulfonylation is carried out, for example, by reacting the compound (IV) wherein Y is an oxygen atom with a sulfonylating agent (e.g. methanesulfonyl chloride, p-toluenesulfonyl chloride, trifluoromethanesulfonyl chloride, trifluoromethanesulfonic anhydride).

The starting compound (IV) may be commercially available ones but can be prepared by a conventional method, for example, by the method disclosed in J. Am. Chem. Soc., 74, 842 (1952), Chem, Ber., 95, 937 (1962), J. Org. Chem., 29, 2887 (1964), or by the methods disclosed in the following Reference Examples 1, 20 and 41-(1), -(3), or by a modified method thereof.

Another starting compound (III) is prepared by a conventional method, for example, by the method disclosed in Japanese Patent First Publication (Kokai) No. 32058/1990, or by the methods disclosed in the following Reference Examples 45, 59 and 70, or by a modified method thereof.

Process (b)

The compound of the formula (I) wherein X is —O— and $R_3$ is a hydrogen atom is prepared by reacting a compound of the formula (II'):

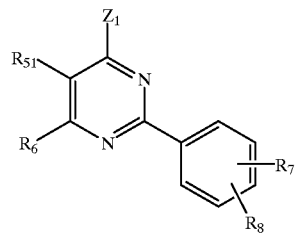

(II')

wherein $Z_1$ is a halogen atom, and $R_{51}$, $R_6$, $R_7$ and $R_8$ are the same as defined above, with a compound of the formula (V):

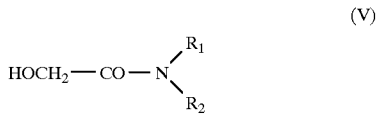

(V)

wherein $R_1$ and $R_2$ are the same as defined above, and if necessary, followed by removing the protecting groups from the product.

The reaction of the compound (II') and the compound (V) is carried out in the presence of a base in a suitable solvent or without a solvent under pressure or under atmospheric pressure. The solvent includes, for example, toluene, xylene, dimethoxyethane, 1,2-dichloroethane, acetone, methyl ethyl ketone, dioxane, diglyme, ethyl acetate, dimethylformamide and dimethylsulfoxide. The base includes, for example, sodium hydride, triethylamine, potassium carbonate, and sodium carbonate. The reaction is usually carried out at a temperature of from about $-10°$ C. to about $150°$ C., preferably at a temperature of from about $10°$ C. to about $70°$ C.

When $R_{51}$ in the product thus obtained has a protecting group, the protecting groups may be removed by hydrogenolysis or hydrolysis, in the same manner as in above Process (a).

The starting compound (V) is prepared by subjecting a compound of the formula (VI):

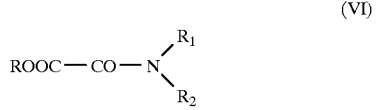

(VI)

wherein R is a lower alkyl group, and $R_1$ and $R_2$ are the same as defined above, to reduction by a conventional method.

The reduction of the compound (VI) is carried out in an alcohol (e.g. methanol, ethanol), an ether (e.g. tetrahydrofuran) or a mixture of these solvents, by using a reducing agent such as lithium borohydride, at a temperature of from about $-5°$ C. to about $0°$ C.

The starting compound (VI) is prepared by a conventional method, or by the method disclosed in the following Reference Example 81-(1), or by a modified method thereof.

Process (c)

The compound of the formula (I) wherein X is —O— is prepared by reacting a compound of the formula (IVa):

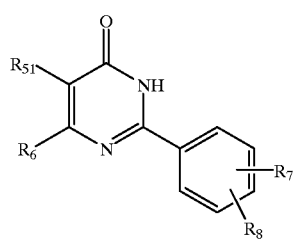

(IVa)

wherein $R_{51}$, $R_6$, $R_7$ and $R_8$ are the same as defined above, with a compound of the formula (VII):

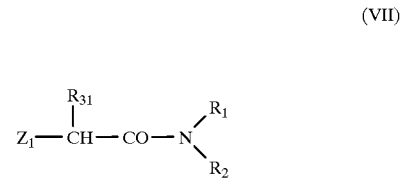

(VII)

wherein $Z_1$, $R_1$, $R_2$ and $R_{31}$ are the same as defined above, if necessary, followed by removing the protecting groups from the product.

The reaction of the compound (IVa) and the compound (VII) is carried out in the same conditions such as solvent, base or reaction temperature, as those in the above Process (b).

When $R_{31}$ and/or $R_{51}$ of the product have a protecting group, the protecting groups may be removed by hydrogenolysis and/or hydrolysis in the same manner as in above Process (a).

The compound (VII) is prepared by a conventional method, for example, by the method disclosed in Japanese Patent First Publication (Kokai) No. 64/1987, or by the method disclosed in the following Reference Example 83, or by a modified method thereof.

Process (d)

The compound of the formula (I) is prepared by reacting a compound of the formula (VIII):

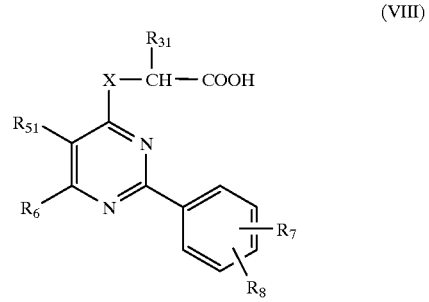

(VIII)

wherein X, $R_{31}$, $R_{51}$, $R_6$, $R_7$ and $R_8$ are the same as defined above, or a reactive derivative thereof, with a compound of the formula (IX):

(IX)

wherein $R_1$ and $R_2$ are the same as defined above, if necessary, followed by removing the protecting groups from the product.

The reactive derivative of the compound (VIII) includes, for example, a lower alkyl ester (e.g. methyl ester), an active ester, an acid anhydride, and an acid halide (e.g. an acid chloride). The active ester includes, for example, p-nitrophenyl ester, 2,4,5-trichlorophenyl ester, and N-hydroxysuccinimide ester. The acid anhydride includes, for example, a symmetric acid anhydride and a mixed acid anhydride. The mixed acid anhydride includes, for example, a mixed acid anhydride with an alkyl chlorocarbonate such as ethyl chlorocarbonate, isobutyl chlorocarbonate, a mixed acid anhydride with an aralkyl chlorocarbonate such as benzyl chlorocarbonate, a mixed acid anhydride with an aryl chlorocarbonate such as phenyl chlorocarbonate, and a mixed acid anhydride with an alkanoic acid such as isovaleric acid and pivalic acid.

When the compound (VIII) per se is used, the reaction can be carried out in the presence of a condensing agent such as N,N'-dicyclohexylcarbodiimide, 1-ethyl-3-(3-dimethylaminopropyl)carbodiimide hydrochloride, N,N'-carbonyldiimidazole, N,N'-carbonyldisuccinimide, 1-ethoxycarbonyl-2-ethoxy-1,2-dihydroquinoline, diphenylphosphoryl azide, propanesulfonic anhydride, and benzotriazol-1-yloxy-tris(dimethylamino) phosphoniumhexafluorophosphate.

The reaction of the compound (VIII) or a reactive derivative thereof with the compound (IX) is carried out in a solvent or without a solvent. The solvent varies according to the kinds of the starting compounds, etc., but includes, for example, aromatic hydrocarbons (e.g. benzene, toluene, xylene), ethers (e.g. diethyl ether, tetrahydrofuran, dioxane), halogenated hydrocarbons (e.g. methylene chloride, chloroform), alcohols (e.g. ethanol, isopropanol), ethyl acetate, acetone, acetonitrile, dimethylformamide, dimethylsulfoxide, ethylene glycol, water, etc., and these solvents may be used alone, or in the form of a mixture of two or more solvents. The reaction is carried out in the presence of a base if necessary, and the base includes, for example, alkali metal hydroxides (e.g. sodium hydroxide, potassium hydroxide), alkali metal carbonates (e.g. sodium carbonate, potassium carbonate), alkali metal hydrogen carbonates (e.g. sodium hydrogen carbonate, potassium hydrogen carbonate), and organic bases such as triethylamine, tributylamine, diisopropylethylamine, N-methylmorpholine, but the excess amount of the compound (IX) may be used instead of a base. The reaction temperature varies according to the kinds of the starting compounds, but it is usually in the range of about $-30°$ C. to about $200°$ C., preferably in the range of about $-10°$ C. to about $150°$ C.

When $R_{31}$ and/or $R_{51}$ of the product thus obtained have a protecting group, these protecting groups may be removed by hydrogenolysis and/or hydrolysis, in the same manner as in above Process (a).

The compound of the formula (VIII) wherein X is an oxygen atom is prepared, for example, by above Process (c), i.e. by reacting the above compound (IVa) with a compound of the formula (X):

(X)

wherein $Z_1$, R and $R_{31}$ are the same as defined above, in the same manner as in Process (c), followed by subjecting the product to hydrolysis in a conventional manner.

The compound of the formula (X) is commercially available ones but can be prepared by a conventional manner.

The compound of the formula (VIII) wherein X is —NH$_4$— is prepared, for example, by above Process (a), i.e. by reacting the compound (II) with a compound of the formula (XI):

(XI)

wherein R' is a lower alkyl group, benzyl group or a benzyl group being substituted by a halogen atom, methyl group or methoxy group, and $R_{31}$ and $R_4$ are the same as defined above, in the same manner as in Process (a), followed by subjecting the product to hydrolysis or hydrogenolysis in a conventional manner.

The compound (XI) is commercially available ones but can be prepared by a conventional method.

Process (e)

The compound of the formula (I) wherein $R_1$ is a lower alkyl group, a lower alkenyl group or a cycloalkyl-lower alkyl group is prepared by reacting a compound of the formula (XII):

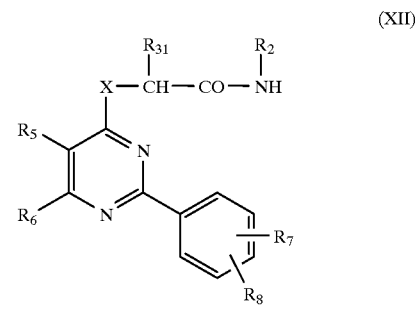

(XII)

wherein X, $R_2$, $R_3$, $R_5$, $R_6$, $R_7$ and $R_8$ are the same as defined above, with a compound of the formula (XIII):

$R_{11}$—$Z_1$   (XIII):

wherein $R_{11}$ is a lower alkyl group, a lower alkenyl group or a cycloalkyl-lower alkyl group, and $Z_1$ is the same as defined above, if necessary, followed by removing the protecting groups from the product.

The reaction of the compound (XII) and the compound (XIII) is usually carried out in a suitable solvent. The solvent includes, for example, aromatic hydrocarbons (e.g. benzene, xylene), ketones (e.g. methyl ethyl ketone), ethers (e.g. dioxane), and dimethylformamide. The reaction is preferably carried out in the presence of a base, and the base includes ones exemplified above in Process (a), and sodium hydride. The reaction temperature varies according to the kinds of the starting compounds or the reaction conditions, but it is usually in the range of about $0°$ C. to about $200°$ C., and when sodium hydride is used as a base, it is in the range of about $0°$ C. to about $50°$ C.

When $R_{31}$ and/or $R_{51}$ of the product have a protecting group, the protecting groups may be removed by hydrogenolysis and/or hydrolysis.

The compound (XII) is prepared by using the compound (VIII) and the compound (IX) wherein $R_1$ is a hydrogen atom in above Process (d).

The compound (XIII) may be commercially available ones but can be prepared by a conventional method.

In above Processes (a) to (e), when the starting compounds used therein have a group which may participate in the reaction, it is convenient to protect said group with a protecting group, or to convert it previously into a group which can easily be converted into said group after the reaction. For example, a part of the compound (I) is prepared by the following processes.

The compound of the formula (I) wherein $R_5$ is an amino group is prepared by subjecting the compound (I) wherein $R_5$ is a nitro group to reduction by a conventional method. This process is explained below in Examples 122 and 124.

The compound of the formula (I) wherein $R_5$ is an acylamino group is prepared by reacting the compound (I) wherein $R_5$ is an amino group with a corresponding carboxylic acid or a reactive derivative thereof. This process is explained below in Example 125.

The compound of the formula (I) wherein $R_5$ is a hydroxy-lower alkyl group is prepared by subjecting the compound (I) wherein $R_5$ is an alkoxycarbonyl group or an alkoxycarbonyl-lower alkyl group wherein the alkyl moiety has carbon atoms fewer by one carbon atom, to reduction by a conventional method. This process is explained below in Example 127.

The compound of the formula (I) wherein $R_8$ is a hydroxy group is prepared by treating the compound (I) wherein $R_8$ is a methoxy group with hydrogen bromide.

The desired compounds obtained in the above Processes can be isolated and purified by a conventional method such as chromatography, recrystallization, re-precipitation, etc. The compound (I) which shows basicity enough to form an acid addition salt thereof is converted into an acid addition salt thereof by treating it with various acids by a conventional method.

Various stereoisomers of the compound (I) can be separated and purified by a conventional method such as chromatography, etc.

The pharmacological activities of the present compounds are explained by the following pharmacological experiments on the representative compounds of the present invention.

Experiment 1: Central ($\omega_1$, $\omega_2$) and peripheral ($\omega_3$) benzodiazepine (BZ) receptor binding assays $BZ\omega_1$ and $BZ\omega_2$ receptor binding assays were carried out according to the method of Stephens, D. N. et al. [cf. J. Pharmacol. Exp. Ther. 253, 334–343 (1990)], and $BZ\omega_3$ receptor binding assay was done according to the method of Schoemaker, H. [cf. J. Pharmacol. Exp. Ther. 225, 61–69 (1983)] each with slight modification.

Receptor membrane fractions for $\omega_1$, $\omega_2$ and $\omega_3$ were prepared from the cerebellum ($\omega_1$), spinal cord ($\omega_1$) or kidney ($\omega_3$) in 7–8 week old male rats of Wistar strain by the procedure described below.

After the cerebellum or spinal cord was homogenized with 20 volumes of ice-cold 50 mM Tris-citrate buffer (pH 7.1), the homogenate was centrifuged for 15 minutes at 40,000 g. The pellet obtained was washed 4 times by the same procedure, frozen and stored for 24 hours at −60° C. The resulting pellet, after being thawed, washed with the buffer and centrifuged, was suspended in the buffer I for the binding assay (50 mM Tris-HCl buffer containing 120 mM NaCl, 5 mM KCl, 2 mM $CaCl_2$ and 1 mM $MgCl_2$; pH 7.4) and the suspension thus obtained (containing 1 g wet tissue/40 ml) was used for the $BZ\omega_1$ and $BZ\omega_2$ receptor binding assays. On the other hand, the kidney was homogenized with 20 volumes of the ice-cold buffer II for the binding assay (50 mM Na—K phosphate buffer containing 100 mM NaCl; pH 7.4), filtered through 4 sheets of gauze, and centrifuged for 20 minutes at 40,000 g. The pellet obtained was suspended in the buffer II and the suspension (containing 1 g wet tissue/100 ml) was used for the binding assay as $BZ\omega_3$ receptor membrane source.

[$^3$H] Flumazenil (final concentration: 0.3 nM for ($\omega_1$ and 1 nM for $\omega_2$) and flunitrazepam (final concentration: 10 $\mu$M) were used for the $BZ\omega_1$ or $BZ\omega_2$ receptor binding assays as the isotope-labeled and unlabeled ligands, respectively. For the $BZ\omega_3$ receptor binding assay, [$^3$H] 4'-chlorodiazepam (7-chloro-1,3-dihydro-1-methyl-5-(4-chlorophenyl)-2H-1, 4-benzodiazepin-2-one) (final concentration: 0.5 nM) and diazepam (final concentration: 100 $\mu$M) were used as the isotope-labeled and unlabeled ligands, respectively. Incubation was performed for 30 minutes at 37° C. in the $BZ\omega_1$ or $BZ\omega_2$ receptor binding assays, and for 150 minutes at 0° C. in the $BZ\omega_3$ receptor binding assay. The $BZ\omega_1$ or $BZ\omega_2$ receptor binding assays were carried out in the presence of bicuculline (final concentration: 100 $\mu$M).

The binding assay was performed by the following procedure. After adding each test compound at certain known concentrations, a [$^3$H] ligand and the buffer I or II to each test tube, each assay was started by addition of membrane preparation (total volume of 1 ml). After incubation, the assay was terminated by filtration with suction through a Whatman GF/B glass fiber filter using a cell harvester (Brandel, USA). The filters were rapidly washed 3 times with 5 ml of ice-cold 50 mM Tris-HCl buffer (pH 7.7) for $\omega_1$ and $\omega_2$, or the buffer II for $\omega_3$, and transferred to scintillation vials containing 10 ml liquid scintillation cocktail (ACS-II, Amersham, USA). After a few hours, retained radioactivity was counted by a liquid scintillation spectrometer. Specific binding of [$^3$H] ligands was calculated as the difference between amounts of radioactivity bound in the presence and absence of excess unlabeled ligands. The concentration of the test compounds causing 50% inhibition of specific binding of the [$^3$H] ligand ($IC_{50}$) was determined by probit analysis. The results of benzodiazepine$\omega_3$ receptor binding assay are shown in Table 5. It is noted that all the compounds listed in Table 5 had affinity for the $BZ\omega_1$ and $BZ\omega_2$ receptors with $IC_{50}$ values larger than 1000 nM.

TABLE 5

| Test Comp. | $\omega_3$ $IC_{50}$ (nM) |
|---|---|
| 1* | 3.10 |
| 2 | 0.97 |
| 4 | 4.36 |
| 5 | 1.28 |
| 6 | 0.23 |
| 10 | 0.70 |
| 15 | 3.86 |
| 16 | 4.00 |
| 17 | 1.97 |
| 22 | 3.26 |
| 23 | 1.76 |
| 25 | 1.93 |
| 26 | 0.28 |
| 27 | 0.11 |
| 29 | 0.85 |
| 35 | 1.51 |
| 36 | 1.44 |
| 37 | 1.66 |
| 41 | 2.53 |
| 42 | 2.15 |
| 44 | 4.98 |
| 45 | 0.70 |
| 47 | 0.16 |
| 49 | 0.23 |
| 51 | 0.32 |
| 52 | 29.5 |
| 57 | 5.39 |
| 58 | 1.62 |
| 61 | 9.80 |
| 65 | 1.66 |
| 68 | 2.19 |
| 69 | 2.75 |
| 70 | 1.12 |
| 76 | 1.33 |
| 79 | 0.87 |
| 81 | 6.90 |
| 83 | 5.02 |
| 84 | 2.04 |
| 85 | 0.18 |
| 93 | 4.10 |
| 97 | 2.27 |
| 102 | 3.31 |
| 103 | 2.90 |
| 104 | 3.44 |

TABLE 5-continued

| Test Comp. | $\omega_3$ IC$_{50}$ (nM) |
|---|---|
| 105 | 4.18 |
| 106 | 4.24 |
| 107 | 4.23 |
| 108 | 1.21 |
| 109 | 2.09 |
| 110 | 1.99 |
| 111 | 2.05 |
| 112 | 2.34 |
| 118 | 1.07 |
| 119 | 1.45 |
| 120 | 1.63 |
| 124 | 5.35 |
| 127 | 4.35 |
| 128 | 0.79 |
| 130 | 1.31 |
| 131 | 0.89 |
| 133 | 2.20 |
| 134 | 3.07 |
| 135 | 3.17 |
| 136 | 0.34 |
| 137 | 0.93 |
| 138 | 0.53 |
| 139 | 0.38 |
| 141 | 0.11 |
| 142 | 0.08 |
| 143 | 1.40 |
| 144 | 0.31 |
| 145 | 1.60 |
| 147 | 0.52 |
| 149 | 1.14 |
| 151 | 0.58 |
| 155 | 0.76 |
| 156 | 4.96 |
| 158 | 4.07 |
| 159 | 2.00 |
| 160 | 4.30 |
| 161 | 1.05 |
| 162 | 1.19 |
| 163 | 2.64 |
| 164 | 0.29 |
| 165 | 5.07 |
| 166 | 5.40 |
| 167 | 0.79 |
| 168 | 0.99 |
| 169 | 1.15 |
| 170 | 0.99 |
| 171 | 1.56 |
| 175 | 1.90 |
| 178 | 0.57 |
| 179 | 4.30 |
| 180 | 1.65 |
| 181 | 1.61 |
| 182 | 4.57 |
| 183 | 8.75 |
| 184 | 0.82 |
| 186 | 2.39 |
| 187 | 9.71 |
| 188 | 5.24 |
| 190 | 4.00 |
| 195 | 2.00 |

*The compound of Example 1 (hereinafter, the compounds of Examples in the same way)

The compounds listed in Table 5 bind strongly to the BZ$\omega_3$ receptor, but have affinity for the BZ$\omega_1$ and B$\omega_2$ receptors with the IC$_{50}$ value larger than 1000 nM. Therefore, it is evident that the compounds of the present invention have potent and highly selective affinity for the BZ$\omega_3$ receptor.

Experiment 2: Light and dark box test (anti-anxiety effect)

Anti-anxiety effect of test compounds was examined in a box with light and dark compartments according to the method of Crawley, J. and Goodwin, F. K. [cf. Pharmacol. Biochem. Behav. 13, 167–170 (1980)] with slight modification.

Light and dark box test is a useful, simple and handy method for behaviorally and pharmacologically examining anti-anxiety effect of the drugs, by utilizing the habit of rodents such as mice and rats, etc. which prefer to stay in a dark place, and regarding as positive drug effect the increase of the relative stay of the animals in the light compartment which is an uncomfortable place for the animals. A number of drugs such as cholecystokinin B type receptor antagonists and BZ anxiolytics, etc. show positive effect in this test.

Light and dark box test was carried out using the test box device (35×15×17 cm) which comprises: a light compartment (20×15×17 cm) consisting of transparent acrylic plates and highly illuminated by an incandescent lamp (1,700 lux); a dark compartment (15×15×17 cm) being made of black acrylic plates connected to the light compartment; and at the boundary of compartments, an opening (4.4×5 cm) in which mice can go through freely between two compartments.

Male mice of Std-ddY strain weighing 25–30 g were used in a group of 10. Each trial was started by placing a mouse in the center of the light compartment 30 minutes after oral administration of a test compound, and the time spent by the mouse in the light compartment during a 5 minute observation period was measured, and the rate of the stay of mice in the light compartment to the whole time spent in the experiment was calculated. The increasing rate of the relative stay of the test compound to that of the vehicle control group was yielded, based on the rate of the stay of mice in the light compartment.

The anti-anxiety effect of the test compound was represented by the minimum effectivetive dose (MED) at which the increasing rate of the relative stay was regarded statistically as significant (Williams-Wilcoxon's test, p<0.05). The results are shown in Table 6.

TABLE 6

| Test Comp. | Anti-anxiety effect MED (mg/kg) |
|---|---|
| 1* | 0.3 |
| 2 | 0.01 |
| 6 | 0.3 |
| 9 | 0.3 |
| 10 | 1.0 |
| 16 | 0.1 |
| 21 | 0.1 |
| 22 | 0.3 |
| 23 | 0.01 |
| 29 | 0.03 |
| 31 | 0.3 |
| 35 | 0.1 |
| 36 | 0.3 |
| 37 | 0.1 |
| 42 | <0.01 |
| 45 | 0.1 |
| 52 | 0.1 |
| 136 | 0.3 |
| 139 | 0.1 |
| 150 | 0.3 |

*The compound of Example 1 (hereinafter, the compounds of Examples in the same way)

Test compounds in Table 6 have anti-anxiety effect at doses of 1 mg/kg or below. Among them, many compounds are effective at doses of 0.3 mg/kg or Experiment 3: Isoniazid-induced clonic convulsion test (anti-convulsant effect)

Isoniazid inhibits glutamate decarboxylase which catalyzes GABA synthesis, deases brain GABA levels, and induces clonic convulsion. According to the method of Auta, J. et al. [cf. J. Pharmacol. Exp. Ther. 265, 649–656 (1993)] with slight modification, we examined antagonistic effect of the test compounds on isoniazid-induced clonic convulsion. Many drugs which, directly or indirectly, enhance $GABA_A$ receptor function are known to exhibit positive effect in this test. Those are BZ anxiolytics represented by diazepam, neurosteroids such as allopregnanolone, allotetrahydrodeoxycortico-sterone(THDOC) and $BZ\omega_3$ receptor agonists which enhance the synthesis of neurosteroids.

Male mice of Std-ddY strain weighing 22–24 g were used in a group of 6. Thirty minutes after oral administration of the test compounds, mice were injected with isoniazid (200 mg/kg, s.c.), and immediately thereafter, placed individually in acrylic observation cages. The onset time of clonic convulsion was measured (cut-off time: 90 minutes). The latency in the control group was about 40 minutes.

Anti-isoniazid effect of the test compounds was expressed as the dose which prolonged the onset time by 25% compared to that in the vehicle group ($ED_{25}$). The $ED_{25}$ value was calculated according to the Litchfield-Wilcoxon's method. The results are shown in Table 7.

TABLE 7

| Test Comp. | Anti-isoniazid effect $ED_{25}$ (mg/kg) |
| --- | --- |
| 1* | 82.2 |
| 2 | 65.6 |
| 4 | 51.2 |
| 5 | 15.1 |
| 9 | 25.5 |
| 10 | 36.9 |
| 11 | 47.5 |
| 12 | 31.8 |
| 17 | 45.7 |
| 21 | 72.1 |
| 22 | 50.3 |
| 23 | 40.8 |
| 25 | 62.1 |
| 29 | 67.5 |
| 35 | 85.7 |
| 36 | 54.2 |
| 37 | 61.9 |
| 42 | 58.7 |
| 44 | 22.4 |
| 45 | 9.60 |
| 47 | 7.62 |
| 48 | 7.67 |
| 50 | 27.3 |
| 52 | 23.5 |
| 53 | 11.3 |
| 58 | 11.8 |
| 59 | 14.8 |
| 60 | 2.14 |
| 61 | 17.7 |
| 65 | 31.1 |
| 66a | 51.2 |
| 66b | 72.4 |
| 79 | 43.8 |
| 83 | 70.2 |
| 171 | 76.4 |

*The compound of Example 1 (hereinafter, the compounds of Examples in the same way)

The test compounds in Table 7 exhibited anti-convulsant effect at doses lower than 100 mg/kg. Some of them caused the effect at doses below 10 mg/kg.

Experiment 4: Collagen-induced arthritis inhibitory test 1

Collagen-induced arthritis inhibitory test is an experimental model for rheumatoid arthritis reported by Trethan, D. E. et al. [cf. J. Exp. Med., 146, 857 (1977)], and thereafter Kakimoto, K. et al. demonstrated that collagen-induced arthritis inhibitory test was useful as an evaluating tool for not only anti-inflammatory agents, but also immuno suppressing agents and immuno modulating agents, based on the mechanism of onset of the disease [cf. J. Immunol., 140, 78–83 (1988)].

Collagen-induced arthritis inhibitory test was carried out according to Kakimoto, K. et al. (cf. above reference of Kakimoto, K. et al.) with slight modification. Solubilized bovine cartilage type II collagen (product of Elastine Products, U.S.A.) was emulsified in complete Freund's adjuvant (product of DIFCO Lab., U.S.A.). Male mice of DBA/1j strain (6 week-old; product of Nippon Charles River, Japan) were immunized by injection at the base of the tail with 150 µg of the emulsified collagen. After twenty one days from the immunization, arthritis was induced by a booster immunization of 150 µg of the emulsified collagen prepared in the same manner as above at the base of the tail again. A test compound was orally administered daily at the dose of 10 mg/kg from the first immunization. Mice were observed daily 5 days after the booster immunization for the onset of arthritis, and an arthritic score was derived by grading the severity of involvement of each paw five scales (0–4) according to the method of Wood, F. D. et al. [cf. Int. Arch. Allergy Appl. Immunol., 35, 456–467 (1969)] with slight modification as shown in Table 8. The severity of arthritis was estimated by the sum of the scores of all 4 paws, and the onset of the disease was determined when score 1 was observed.

TABLE 8

| Score | Symptoms |
| --- | --- |
| 0 | No changes |
| 1 | Erythema and swelling of one interphalangeal joint of the fingers of 4 paws |
| 2 | Erythema and swelling of two or more interphalangeal joints, or relatively large joints of wrist, ankle, etc. |
| 3 | Gross swelling and erythema |
| 4 | Reaching the maximum level of swelling of the entire paw |

In the mice which were administered with the compound of Example 93, the onset of arthritis was delayed until 40 days, after the booster immunization, while in the control mice which were injected with the solvent, the onset of arthritis was observed on 28th day. In the mice which were administered with the compound of Example 136 and Example 144, the onset of arthritis was delayed until 34 days and 37 days, respectively, after the booster immunization. The severity of arthritis in the compound-treated group (Example 93, 136 and 144) was much lower than the control group in the severity of the disease judging from the score of arthritis.

Experiment 5: Collagen-induced arthritis inhibitory test 2

Collagen-induced arthritis inhibitory test was carried out according to Kakimoto, K. et al. (cf. above reference of Kakimoto, K. et al.) with slight modification. Type II collagen from bovine joints (product of the Collagen Research Center, Japan) was emulsified in complete Freund's adjuvant (product of DIFCO Lab., U.S.A.). Female mice of DBA/1j strain (product of Nippon Charles River, Japan) were immunized by injection at the base of the tail with 150 µg of the emulsified collagen. After twenty one days from the immunization, arthritis was induced by a booster immunization of 150 µg of the emulsified collagen prepared in the same manner as above at the base of the tail again. Test compounds were administered orally at a dose of 10 mg/kg on 5 consecutive days in a week for 8 weeks, beginning from the day before the immunization. Mice were monitored visually for arthritis once a week beginning from the day of the booster immunization. Each paw was individually scored on a scale of 0–3, according to the criteria shown in Table 9. The severity of arthritis was estimated by the sum of the scores of all 4 paws.

TABLE 9

| Score | Symptoms |
|---|---|
| 0 | No changes |
| 1 | Erythema and swelling of one or more interphalangeal joints of the paw |
| 2 | Erythema and swelling of two or more large joints which extends to the back of the paw in addition to Erythema and swelling of one or more interphalangeal joints of the paw |
| 3 | Severe erythema and swelling of the entire paw |

In the mice which were administered with the compound of Example 6, the onset of arthritis was delayed until 21 days after the booster immunization as compared with the control mice which were injected with the solvent, and the severity of arthritis in the compound-treated group was much lower than the control group at least until day 34, the last day of the experiment. The compound of Example 165 markedly suppressed the arthritis as compared with control group, at least until 34th day, the last day of the experiment. In the mice which were administered with the compound of Example 178, the arthritis was suppressed as compared with the control.

From the results clearly shown in the above experiments 4 and 5, the compounds of Examples 6, 93, 136, 144 and 165 exhibit potent effect on collagen-induced arthritis inhibitory test which is a model for immuno inflammatory diseases (rheumatoid arthritis, etc.). The compound of Example 178 has also effect, but less potent effect as compared with that of each compound as indicated above.

Experiment 6: Acute toxicity

Male mice of Std-ddY strain weighing 24–31 g were used in a group of 10 for examining acute toxicity of test compounds (Example 2, 10, 23, 36, 42 and 52). A compound (1000 mg/kg) was suspended in 0.5% tragacanth and administered orally or intraperitoneally. Then, lethality of the mice was observed for 7 days after the treatment.

No lethality was found in mice to which the test compound was administered.

The compound of formula (I) and its pharmaceutically acceptable salts not only bind to the $BZ\omega_3$ receptor selectively and strongly, but also produce excellent pharmacological effects such as anti-anxiety effect and anti-convulsant effect, etc. in animal experiment, therefore, are useful for the therapy or prevention of CNS diseases [anxiety-related diseases (neurosis, somatoform disorders, other anxiety disorders), depression, epilepsy, etc.] and cardiovascular diseases (cardiac angina, hypertension, etc.).

There are listed, for example, the following compounds and pharmaceutically acceptable salts thereof which show not only selective and strong affinity for $BZ\omega_3$ receptor, but also strong anti-anxiety effect.

(1) 2-[2-(4-Chlorophenyl)-5,6-dimethyl-4-pyrimidinylamino]-N,N-dipropylacetamide (the compound of Example 2)

(2) 2-[2-(4-Chlorophenyl)-5,6-dimethyl-4-pyrimidinylamino]-N-methyl-N-phenylacetamide (the compound of Example 23)

(3) 2-[2-(4-Chlorophenyl)-5,6-dimethyl-4-pyrimidinylamino]-N,N-diethylacetamide (the compound of Example 10)

(4) N-(4-Chlorophenyl)-N-methyl-2-(5,6-dimethyl-2-phenyl-4-pyrimidinylamino) acetamide (the compound of Example 29)

(5) 2-[2-(4-Chlorophenyl)-5,6-dimethyl-4-pyrimidinylamino]-N-(4-fluorophenyl)-N-methylacetamide (the compound of Example 36)

(6) 2-[2-(4-Chlorophenyl)-5,6-dimethyl-4-pyrimidinylamino]-N-(4-methoxyphenyl)-N-methylacetamide (the compound of Example 42)

(7) 2-(5,6-Dimethyl-2-phenyl-4-pyrimidinylamino)-N-phenyl-N-propylacetamide (the compound of Example 52)

(8) 2-[2-(4-Chlorophenyl)-5,6-dimethyl-4-pyrimidinylamino]-N-ethyl-N-phenylacetamide (the compound of Example 45)

The compounds of formula (I) have inhibitory effect on collagen-induced arthritis, therefore, are useful for the therapy or prevention of immune diseases such as immuno inflammatory diseases (rheumatoid arthritis, etc.) and immunoneurologic diseases (multiple sclerosis, etc.).

There are listed, for example, the following compounds and pharmaceutically acceptable salts thereof which show inhibitory effect on collagen-induced arthritis.

(1) 2-(5,6-Dimethyl-2-phenyl-4-pyrimidinyloxy)-N,N-dipropylacetamide (the compound of Example 136)

(2) 2-(2,6-Diphenyl-4-pyrimidinylamino)-N,N-dipropylacetamide (the compound of Example 93)

(3) 2-[5,6-Dimethyl-2-(4-trifluoromethylphenyl)-4-pyrimidinylamino]-N,N-dipropylacetamide (the compound of Example 6)

(4) 2-[2-(4-Aminophenyl)-5,6-dimethyl-4-pyrimidinyloxy]-N-ethyl-N-phenylacetamide (the compound of Example 165)

(5) 2-[2-(4-Chlorophenyl)-5,6-dimethyl-4-pyrimidinyloxy]-N-methyl-N-phenylacetamide (the compound of Example 144)

(6) 2-(5,6-Dimethyl-2-phenyl-4-pyrimidinyloxy)-N-phenyl-N-propylacetamide (the compound of Example 178)

The compounds [I] of the present invention or a pharmaceutically acceptable acid addition salt thereof can be administered either orally, parenterally or rectally. The dose of the compounds of the present invention varies according to the kinds of the compound, the administration routes, the conditions, ages of the patients, etc., but it is usually in the range of 0.01–50 mg/kg/day, preferably in the range of 0.03–5 mg/kg/day.

The compounds of the present invention is usually administered in the form of a pharmaceutical preparation which is prepared by mixing thereof with a pharmaceutically acceptable carrier or diluent. The pharmaceutically acceptable carrier or diluent may be any conventional ones which are usually used in the pharmaceutical field, and do not react with the compounds of the present invention. Suitable examples of the pharmaceutically acceptable carrier or diluent are, for example, lactose, inositol, glucose, mannitol, dextran, cyclodextrin, sorbitol, starch, partly pregelatinized starch, white sugar, magnesium metasilicate aluminate, synthetic aluminum silicate, crystalline cellulose, sodium carboxymethylcellulose, hydroxypropyl starch, calcium carboxylmethylcellulose, ion exchange resin, methylcellulose, gelatin, gum arabic, hydroxypropyl cellulose, low substituted hydroxypropyl cellulose, hydroxypropylmethylcellulose, polyvinylpyrrolidone, polyvinyl alcohol, alginic acid, sodium alginate, light anhydrous silicic acid, magnesium stearate, talc, carboxyvinyl polymer, titanium oxide, sorbitan fatty acid ester, sodium laurylsulfate, glycerin, glycerin fatty acid ester, purified lanolin, glycerogelatin, polysorbate, macrogol, vegetable oil, wax, propyleneglycol, water, ethanol, polyoxyethylene-hydrogenated caster oil (HCO), sodium chloride, sodium hydroxide, hydrochloric acid, disodium hydrogen phosphate, sodium dihydrogen phosphate, citric acid, glutamic acid, benzyl alcohol, methyl p-oxybenzoate, ethyl p-oxybenzoate, etc.

The pharmaceutical preparation is, for example, tablets, capsules, granules, powders, syrups, suspensions, suppositories, injection preparations, etc. These preparations may be prepared by a conventional method. In the preparation of liquids, the compound of the present invention may be dissolved or suspended in water or a suitable other solvent, when administered. Tablets and granules may be coated by a conventional method. In the injection preparations, it is preferable to dissolve the compound of the present invention in water, but if necessary, it may be dissolved by using an isotonic agent or a solubilizer, and further, a pH adjustor, a buffering agent or a preservative may be added thereto.

These preparations may contain the compound of the present invention at a ratio of at least 0.01%, preferably at a ratio of 0.1–70%. These preparations may also contain other therapeutically effective compounds as well.

BEST MODE FOR CARRYING OUT THE INVENTION

The present invention is illustrated in more detail by the following Reference Examples and Examples, but should not be construed to be limited thereto.

The identification of the compounds is carried out by Elementary analysis, Mass spectrum, IR spectrum, NMR spectrum, etc.

The following abbreviations may be used in the following Reference Examples and Examples in order to simplify the disclosure.

[Solvent for recrystallization]
A: Ethanol
AC: Acetonitrile
E: Diethyl ether
EA: Ethyl acetate
HX: n-Hexane
IP: Isopropanol
M: Methanol

REFERENCE EXAMPLE 1

Preparation of 5,6-dimethyl-2-phenyl-4(3H)-pyrimidinone:

To a mixture of sodium ethoxide (31.3 g) and anhydrous ethanol (200 ml) is added benzamidine hydrochloride (23.9 g) at 0–5° C. The mixture is stirred at 0° C. for 30 minutes, and thereto is added dropwise a solution of ethyl 2-methylacetoacetate (20 g) and anhydrous ethanol (50 ml) at the same temperature. After addition, the mixture is stirred at room temperature for 30 minutes, and refluxed for six hours. The reaction mixture is concentrated under reduced pressure, and the residue is dissolved in water. The pH value of the mixture is adjusted to pH 4 by addition of conc. hydrochloric acid while the mixture is stirred at 0–5° C. The precipitates are collected by filtration, washed with water, further washed with diethyl ether, and recrystallized from ethanol to give the desired compound (14.3 g), m.p. 205–207° C.

REFERENCE EXAMPLES 2–19

The corresponding starting compounds are treated in the same manner as in Reference Example 1 to give the compounds as listed in Table 10.

TABLE 10

| Ref. Ex. | $R_5$ | $R_6$ | $R_7$ | M.p. (°C.) | Solv. for recrystal. |
|---|---|---|---|---|---|
| 2 | Me | Me | 4-Cl | 258–260 | M |
| 3 | Me | Me | 3-Cl | 251–252 | A |
| 4 | Me | Me | 4-F | 266–268 | M |
| 5 | Me | Me | 4-OMe | 233–235 | M |
| 6 | Me | Me | 4-CF$_3$ | 265–267 | M |
| 7 | Me | Me | 4-NO$_2$ | >300 | M |
| 8 | Me | Et | H | 195–197 | M |
| 9 | Me | i-Pr | H | 230–232 | M |
| 10 | Et | Me | H | 159–161 | A |
| 11 | H | Me | H | 212–214 | A |
| 12 | H | CF$_3$ | H | 228–230 | A |
| 13 | H | Ph | H | 281–284 | A |
| 14 | H | Ph | 4-Cl | >300 | M |
| 15 | Me | Ph | H | 250–252 | M |
| 16 | Me | Ph | 4-Cl | 293–295 | M |
| 17 | —(CH$_2$)$_4$— | | H | 223–225 | A |
| 18 | —(CH$_2$)$_4$— | | 4-Cl | 290–292 | M |
| 19 | COOEt | H | H | 237–238 | A |

REFERENCE EXAMPLE 20

Preparation of 5-nitro-2-phenyl-4(3H)-pyrimidinone:

To a mixture of sodium methoxide (8 g) and anhydrous ethanol (100 ml) is added benzamidine hydrochloride (11.7 g) at 0° C. The mixture is stirred at 0° C. for 30 minutes, and thereto is added dropwise a solution of crude ethyl 2-(N,N-dimethylaminomethylene)nitroacetate (14 g), which is obtained by refluxing a mixture of ethyl nitroacetate (10 g) and N,N-dimethylformamide dimethyl acetal (10.7 g) for three hours, followed by concentrating the mixture under reduced pressure, in anhydrous ethanol (50 ml) at the same temperature. After addition, the mixture is stirred at room temperature for 30 minutes, and refluxed for 12 hours. The reaction mixture is concentrated under reduced pressure, and water (150 ml) is added to the residue. The pH value of the mixture is adjusted to pH 4 by addition of conc. hydrochloric acid while the mixture is stirred at 0° C. The precipitates are collected by filtration, washed with water, and recrystallized from ethanol to give the desired compound (7 g), m.p. 264–266° C.

REFERENCE EXAMPLE 21

Preparation of 4-chloro-5,6-dimethyl-2-phenylpyrimidine:

A mixture of 5,6-dimethyl-2-phenyl-4(3H)-pyrimidine (10 g) and phosphorus oxychloride (23 g) is stirred at 75° C. for four hours. The reaction mixture is concentrated under reduced pressure, and the residue is dissolved in chloroform. To the mixture is added ice-water, and the mixture is stirred. The mixture is neutralized with 1N aqueous sodium hydroxide solution, and the chloroform layer is collected, dried over anhydrous sodium sulfate, and concentrated under reduced pressure. The residue is recrystallized from ethanol to give the desired compound (10.7 g), m.p. 120–122° C.

REFERENCE EXAMPLES 22–40

The corresponding starting compounds are treated in the same manner as in Reference Example 21 to give the compounds as listed in Table 11.

TABLE 11

| Ref. Ex. | $R_5$ | $R_6$ | $R_7$ | M.p. (°C.) | Solv. for Recrystal. |
|---|---|---|---|---|---|
| 22 | Me | Me | 4-Cl | 122–124 | IP |
| 23 | Me | Me | 3-Cl | 96–97 | A |
| 24 | Me | Me | 4-F | 138–139 | IP |
| 25 | Me | Me | 4-OMe | 106–108 | IP |
| 26 | Me | Me | 4-CF$_3$ | 70–71 | IP |
| 27 | Me | Me | 4-NO$_2$ | 157–158 | A |
| 28 | Me | Et | H | 87–88 | IP |
| 29 | Me | i-Pr | H | 83–84 | IP |
| 30 | Et | Me | H | 57–58 | IP |
| 31 | H | Me | H | 62–63 | IP |
| 32 | H | CF$_3$ | H | 45–46 | IP |
| 33 | H | Ph | H | 99–100 | IP |
| 34 | H | Ph | 4-Cl | 125–126 | IP |
| 35 | Me | Ph | H | 116–117 | IP |
| 36 | Me | Ph | 4-Cl | 126–128 | IP |
| 37 | —(CH$_2$)$_4$— | | H | 100–101 | IP |
| 38 | —(CH$_2$)$_4$— | | 4-Cl | 114–115 | IP |
| 39 | NO$_2$ | H | H | 160–161 | A |
| 40 | COOEt | H | H | 39–40 | HX |

REFERENCE EXAMPLE 41

Preparation of 4-chloro-2-(4-fluorophenyl)-5,6,7,8-tetrahydroquinozoline:

(1) A mixture o 4-fluorobenzoyl chloride (50 g), potassium thiocyanate (36.7 g) and anhydrous toluene (100 ml) is refluxed for six hours. After cooling, the reaction mixture is filtered, and the filtrate is concentrated under reduced pressure. The residue is purified by distillation under reduced pressure to give 4-fluorobenzoyl isothiocyanate (55 g), b.p. 92° C/3 mmHg.

(2) To a mixture of the above product (62 g) and chloroform (80 ml) is added dropwise a solution of 1-morpholinocyclohexene (28.6 g) and chloroform (30 ml) with stirring while the temperature of the mixture is kept at 0–5° C. After addition, the reaction mixture is stirred at 0° C. for one hour, and further stirred at room temperature for one hour, and refluxed for one hour. The reaction mixture is concentrated under reduced pressure, and the residue is purified by silica gel column chromatography (eluent; chloroform), and recrystallized from ethanol to give 2-(4-fluorophenyl)-5,6,7,8-tetrahydro-4H-1,3-benzoxazine-4-thione (24 g), m.p. 148–149° C.

(3) Into a mixture of the above product (20 g) and methanol (300 ml) is blown ammonia gas for 30 minutes, and the mixture is stirred at 80° C. for 30 minutes. The reaction mixture is concentrated under reduced pressure, and the residue is recrystallized from ethanol to give 2-(4-fluorophenyl)-5,6,7,8-tetrahydro-4(3H)-quinazolinethione (18 g), m.p. 198–200° C.

(4) A mixture of the above product (10 g) and phosphorus oxychloride (30 g) is refluxed for two hours. The reaction mixture is concentrated under reduced pressure, and the residue is dissolved in chloroform. To the mixture is added ice-water, and the mixture is stirred. The chloroform layer is collected, dried over anhydrous sodium sulfate, and concentrated under reduced pressure. The residue is recrystallized from isopropanol to give the desired compound (8.5 g), m.p. 96–97° C.

REFERENCE EXAMPLES 42–44

The same procedures as Reference Example 41 are repeated except that the corresponding starting compounds are used instead of 4-fluorobenzoyl chloride to give the following compounds.

(Reference Example 42)
  4-Chloro-2-(2-chlorophenyl)-5,6,7,8-tetrahydroquinazoline; m.p. 79–80° C.

(Reference Example 43)
  4-Chloro-2-(3-chlorophenyl)-5,6,7,8-tetrahydroquinazoline; m.p. 94–95° C.

(Reference Example 44)
  4-Chloro-2-(2,4-difluorophenyl)-5,6,7,8-tetrahydroquinazoline; m.p. 57–58° C.

REFERENCE EXAMPLE 45

Preparation of 2-amino-N,N-dipropylacetamide:

(1) To a mixture of dipropylamine (5 g), triethylamine (5 g) and methylene chloride (50 ml) is added dropwise a solution of N-phthaloylglycyl chloride (11 g) in methylene chloride (50 ml) while the temperature of the mixture is kept at 0–5° C. After addition, the mixture is stirred at room temperature for six hours. To the reaction mixture is added water, and the methylene chloride layer is collected, dried over anhydrous sodium sulfate, and concentrated under reduced pressure. The residue is recrystallized from isopropanol to give 2-phthalimide-N,N-dipropylacetamide (12.5 g), m.p. 99–100° C.

(2) A mixture of the above product (12.5 g), hydrazine • monohydrate (4.3 g) and ethanol (150 ml) is refluxed for one hour. The reaction mixture is concentrated under reduced pressure, and chloroform is added to the residue. The mixture is filtered, and to the filtrate is added water. The chloroform layer is collected, dried over anhydrous sodium sulfate, and concentrated under reduced pressure to give the desired compound (6.7 g) as an oily product.

REFERENCE EXAMPLES 46–58

The corresponding starting amine compounds are treated in the same manner as in reference Example 45 to give the compounds as listed in Table 12.

TABLE 12

$$H_2N-CH_2-CO-N\begin{smallmatrix}R_1\\R_2\end{smallmatrix}$$

| Ref. Ex. | $R_1$ | $R_2$ |
|---|---|---|
| 46 | Me | Me |
| 47 | Et | Et |
| 48 | i-Pr | i-Pr |
| 49 | Bu | Bu |
| 50 | Me | i-Bu |
| 51 | Et | Pr |
| 52 | H | Ph |
| 53 | Me | Ph |
| 54 | Et | Ph |
| 55 | Bw | Ph |

TABLE 12-continued $$H_2N-CH_2-CO-N\diagup^{R_1}_{R_2}$$

| Ref. Ex. | $R_1$ | $R_2$ |
|---|---|---|
| 56 | Pr | Ph |
| 57 | Me | Ph-4-Cl |
| 58 | Me | Ph-4-OMe |

REFERENCE EXAMPLE 59

Preparation of 2-amino-N-(4-fluorophenyl)-N-methylacetamide:

(1) The same procedure as Reference Example 45-(1) are repeated except that 4-fluoroaniline (15 g) is used instead of dipropylamine. The product thus obtained is purified by silica gel column chromatography (eluent; chloroform), and recrystallized from ethanol to give N-(4-fluorophenyl)-2-phthalimidacetamide (19 g), m.p. 212–214° C.

(2) The above product (18 g) is added to a mixture of sodium hydride (about 60% oily, 3 g) and dimethylformamide (100 ml) at 0–5° C., and the mixture is stirred at 0° C. for one hour. To the mixture is added dropwise methyl iodide (10 g) at the same temperature. After addition, the mixture is stirred at room temperature for 8 hours. To the reaction mixture are added water and chloroform, and the chloroform layer is collected, dried over anhydrous sodium sulfate, and concentrated under reduced pressure. The residue is purified by silica gel column chromatography (eluent; chloroform), and recrystallized from ethanol to give N-(4-fluorophenyl)-N-methyl-2-phthalimidacetamide (15 g), m.p. 182–183° C.

(3) The above product (14 g) is treated in the same manner as in Reference Example 45-(2) to give the desired compound (9.0 g) as an oily product.

REFERENCE EXAMPLE 60

Preparation of N-allyl-2-amino-N-phenylacetamide:

The same procedures as Reference Example 59 are repeated except that aniline and allyl bromide are used instead of 4-fluoroaniline in Reference Example 59-(1) and methyl iodide in Reference Example 59-(2), respectively, to give the desired compound as an oily product.

REFERENCE EXAMPLE 61

Preparation of 2-amino-N-cyclopropylmethyl-N-phenylacetamide:

The same procedures as Reference Example 59 are repeated except that aniline and cyclopropylmethyl bromide are used instead of 4-fluoroaniline in Reference Example 59-(1) and methyl iodide in Reference Example 59-(2), respectively, to give the desired compound as an oily product.

REFERENCE EXAMPLES 62–66

The corresponding starting compounds are treated in the same manner as in Reference Example 59 to give the following compounds.
(Reference Example 62)
2-Amino-N-(4-bromophenyl)-N-methylacetamide
(Reference Example 63)
2-Amino-N-(2-chlorophenyl)-N-methylacetamide
(Reference Example 64)
2-Amino-N-(3-chlorophenyl)-N-methylacetamide
(Reference Example 65)
2-Amino-N-(4-chlorophenyl)-N-ethylacetamide
(Reference Example 66)
2-Amino-N-(4-chlorophenyl)-N-propylacetamide

REFERENCE EXAMPLES 67–69

The corresponding starting amine compounds are treated in the same manner as in Reference Example 45 to give the following compounds.
(Reference Example 67)
1-Aminoacetyl-3,5-dimethylpiperidine
(Reference Example 68)
4-Aminoacetyl-2,6-dimethylmorpholine
(Reference Example 69)
1-Aminoacetyl-cis-3,5-dimethylpiperazine

REFERENCE EXAMPLE 70

Preparation of N-(4-chlorophenyl)-N-methyl-2-methylaminoacetamide:

(1) To a mixture of N-(tert-butoxycarbonyl)-N-methylglycine (10 g), 4-chloroaniline (8.8 g), benzotriazol-1-yloxy-tris(dimethylamino)phosphonium hexafluorophosphate (BOP reagent, 25.7 g) and methylene chloride (150 ml) is added dropwise triethylamine (5.9 g) while the temperature of the mixture is kept at 0–5° C. After addition, the mixture is stirred at room temperature for 8 hours, and thereto is added water. The methylene chloride layer is collected, dried over anhydrous sodium sulfate, and concentrated under reduced pressure. The residue is purified by silica gel column chromatography (eluent; chloroform), and recrystallized from diethyl ether to give 2-[N'-(tert-butoxycarbonyl)-N'-methylamino]-N-(4-chlorophenyl) acetamide, m.p. 126–128° C.

(2) The above product (12 g) is added to a mixture of sodium hydride (about 60% oily, 3.2 g) and dimethylformamide (100 ml) at 0–5° C., and the mixture is stirred at 0° C. for one hour, and then thereto is added methyl iodide (17 g) at the same temperature. After addition, the mixture is stirred at room temperature for 8 hours, and thereto are added water and chloroform. The chloroform layer is collected, dried over anhydrous sodium sulfate, and concentrated under reduced pressure. The residue is purified by silica gel column chromatography (eluent; chloroform) to give 2-[N'-(tert-butoxycarbonyl)-N'-methylamino]-N-(4-chlorophenyl)-N-methylacetamide (11.4 g) as an oily product.

(3) To a mixture of the above product (8.4 g) and methylene chloride (100 ml) is added dropwise trifluoroacetic acid (20 ml) at 0–5° C. After addition, the mixture is stirred at room temperature for three hours. The reaction mixture is concentrated under reduced pressure, and to the residue is added water. The mixture is made weak basic with 1N aqueous sodium hydroxide solution while the mixture is stirred under ice-cooling, and then thereto is added chloroform. The chloroform layer is collected, dried over anhydrous sodium sulfate, and concentrated under reduced pressure to give the desired compound (4.7 g) as an oily product.

REFERENCE EXAMPLES 71–73

The corresponding starting tert-butoxycarbonylated amino acids are treated in the same manner as in Reference Example 70 to give the following compounds as an oily product.
(Reference Example 71)
N-(4-Chlorophenyl)-N-methyl-2-pyrrolidinecarboxyamide
(Reference Example 72)
N-(4-Chlorophenyl)-N-methyl-2-piperidinecarboxyamide (Reference Example 73)
    N-(4-Chlorophenyl)-2,3-dihydro-N-methyl-1H-indole-2-carboxyamide

REFERENCE EXAMPLES 74–80

The corresponding starting tert-butoxycarbonylated amino acids are treated in the same manner as in Reference Example 70-(1), -(3) to give the following compounds as an oily product.
(Reference Example 74)
    2-Amino-3-benzyloxy-N,N-dipropylpropanamide
(Reference Example 75)
    2-Methylamino-N,N-dipropylacetamide
(Reference Example 76)
    2-Ethylamino-N,N-dipropylacetamide
(Reference Example 77)
    2-Methylamino-N-methyl-N-phenylacetamide
(Reference Example 78)
    2-Ethylamino-N-methyl-N-phenylacetamide
(Reference Example 79)
    N,N-Dipropyl-2-pyrrolidinecarboxamide
(Reference Example 80)
    2,3-Dihydro-N,N-dipropyl-1H-indolecarboxamide

REFERENCE EXAMPLE 81

Preparation of 2-hydroxy-N,N-dipropylacetamide:

(1) To a mixture of dipropylamine (5.0 g), triethylamine (5.5 g) and methylene chloride (70 ml) is added dropwise a solution of ethyloxalyl chloride (7.4 g) and methylene chloride (30 ml) with stirring while the temperature of the mixture is kept at −20° C. After addition, the mixture is stirred at 0° C. for four hours. To the reaction mixture is added water, and the methylene chloride layer is collected, dried over anhydrous sodium sulfate, and concentrated under reduced pressure to give ethyl 2-oxo-2-(N,N-dipropylamino)acetate (9.5 g) as an oily product.

(2) A mixture of the above product, sodium borohydride, lithium chloride and anhydrous tetrahydrofuran is stirred at room temperature for 30 minutes, and thereto is added dropwise anhydrous ethanol while the temperature of the mixture is kept at 0–5° C. After addition, the mixture is stirred at room temperature for 12 hours. The reaction mixture is cooled to 0° C., an the pH value thereof is adjusted to pH 5 with 1N hydrochloric acid, and concentrated under reduced pressure. To the residue are added a saturated brine and chloroform, and the chloroform layer is collected, dried over anhydrous sodium sulfate, and concentrated under reduced pressure to give the desired compound (7.7 g) as an oily product.

REFERENCE EXAMPLE 82

Preparation of N,N-dibutyl-2-hydroxyacetamide:

The same procedures as Reference Example 81 are repeated except that dibutylamine is used instead of dipropylamine to give the desired compound as an oily product.

REFERENCE EXAMPLE 83

Preparation of 2-bromo-N,N-dipropylacetamide:

To a mixture of dipropylamine (10.1 g), triethylamine (10.1 g) and anhydrous diethyl ether (80 ml) is added dropwise a solution of bromoacetyl chloride (15.8 g) in anhydrous diethyl ether (40 ml) while the temperature of the mixture is kept at −40° C. After addition, the temperature is gradually raised, and the mixture is stirred at room temperature for one hour. The reaction mixture is filtered, and the filtrate is concentrated under reduced pressure, and purified by distillation under reduced pressure to give the desired compound (14 g), b.p. 100–103° C./1 mmHg.

REFERENCE EXAMPLES 84–87

The corresponding starting compounds are treated in the same manner as in Reference Example 83 to give the following compounds.
(Reference Example 84)
    2-Bromo-N,N-dipropylpropanamide; b.p. 85–87° C./I1 mmHg
(Reference Example 85)
    2-Bromo-N-(4-chlorophenyl)-N-methylacetamide; m.p. 52–53° C.
(recrystallized from isopropanol)
(Reference Example 86)
    2-Bromo-N-methyl-N-phenylpropanamide; b.p. 135–145° C./1 mmHg
(Reference Example 87)
    2-Bromo-N-ethyl-N-phenylpropanamide; oily product

REFERENCE EXAMPLE 88

Preparation of 2-(5,6-dimethyl-2-phenyl-4-pyrimidinyloxy) acetic acid:

(1) To a mixture of sodium hydride (about 60% oily, 1.0 g) and dimethylformamide (80 ml) is added 5,6-dimethyl-2-phenyl-4(3H)-pyrimidinone (5.0 g) while the temperature of the mixture is kept at 0–5° C., and the mixture is stirred at 0° C. for 30 minutes. To the mixture is added dropwise ethyl bromoacetate (4.2 g) at the same temperature. After addition, the mixture is stirred at 80° C. for three hours, and thereto are added ice-water and chloroform. The chloroform layer is collected by filtration, washed with water, dried over anhydrous sodium sulfate, and concentrated under reduced pressure. The residue is purified by silica gel column chromatography (eluent; chloroform), and recrystallized from isopropanol to give ethyl 2-(5,6-dimethyl-2-phenyl-4-pyrimidinyloxy)acetate (6.2 g), m.p. 90–91° C.

(2) A mixture of the above product (6.0 g), 1N aqueous sodium hydroxide solution (100 ml) and ethanol (50 ml) is stirred at room temperature for 8 hours. The reaction mixture is concentrated under reduced pressure, and the residue is dissolved in ice-water. The pH value of the mixture is adjusted to pH 1 with conc. hydrochloric acid, and the precipitates are collected by filtration, washed with water, and recrystallized from ethanol to give the desired compound (3.5 g), m.p. 175–177° C.

REFERENCE EXAMPLES 89–90

The corresponding starting compounds are treated in the same manner as in Reference Example 88, and the products thus obtained are recrystallized from ethanol to give the following compounds.
(Reference Example 89)
    2-(5,6,7,8-Tetrahydro-2-phenyl-4-quinazolinyloxy)acetic acid; m.p. 155–157° C.
(Reference Example 90)
    2-[2-(4-Chlorophenyl) -5,6,7,8-tetrahydro-4-quinazolinyloxy) acetic acid; m.p. 195–197° C.

REFERENCE EXAMPLES 91–92

The corresponding starting t-butoxycarbonylated amino acids are treated in the same manner as in Reference Example 70 to give the following compounds as an oily product.
(Reference Example 91)
    2-Methylamino-N-phenyl-N-propylacetamide
(Reference Example 92)
    N-Allyl-2-methylamino-N-phenylacetamide

REFERENCE EXAMPLES 93–94

The corresponding starting t-butoxycarbonylated amino acids are treated in the same manner as in Reference Example 70-(1) and -(3) to give the following compounds as an oily product.
(Reference Example 93)
  N,N-Diethyl-2-methylaminoacetamide
(Reference Example 94)
  N-Ethyl-2-methylamino-N-phenylacetamide

EXAMPLE 1

Preparation of 2-(5,6-dimethyl-2-phenyl-4-pyrimidinylamino)-N,N-dipropylacetamide:

A mixture of 4-chloro-5,6-dimethyl-2-phenylpyrimidine (1.0 g), 2-amino-N,N-dipropylacetamide (0.87 g) and triethylamine (0.55 g) is refluxed with stirring at 150° C. for three hours. To the reaction mixture are added water and chloroform, and the chloroform layer is collected, dried over anhydrous sodium sulfate, and concentrated under reduced pressure. The residue is purified by silica gel column chromatography (eluent; chloroform), and recrystallized from a mixture of diethyl ether and n-hexane to give the desired compound (1.3 g), m.p. 79–80° C.

EXAMPLES 2–63

The corresponding starting compounds are treated in the same manner as in Example 1 to give the compounds as listed in Table 13.

TABLE 13

| Ex. | $R_1$ | $R_2$ | $R_7$ | Q | M.p. (°C.) | Solv. for recrystal. |
|---|---|---|---|---|---|---|
| 2 | Pr | Pr | 4-Cl | | 74–75 | E-HX |
| 3 | Pr | Pr | 3-Cl | | 101–103 | IP |
| 4 | Pr | Pr | 4-F | | 70–71 | E-HX |
| 5 | Pr | Pr | 4-OMe | | 83–85 | IP |
| 6 | Pr | Pr | 4-$CF_3$ | | 83–85 | HX-EA |
| 7 | Pr | Pr | 4-$NO_2$ | | 135–137 | IP |
| 8 | Me | Me | H | | 174–175 | IP |
| 9 | Et | Et | H | | 113–114 | E-HX |
| 10 | Et | Et | 4-Cl | | 152–153 | IP |
| 11 | Et | Et | 4-F | | 139–140 | IP |
| 12 | Et | Et | 4-OMe | | 130–132 | IP |
| 13 | i-Pr | i-Pr | H | | 171–172 | IP |
| 14 | Bu | Bu | H | | 46–47 | HX |
| 15 | Bu | Bu | 4-Cl | | 52–53 | HX |
| 16 | Bu | Bu | 4-F | | 45–46 | HX |
| 17 | Et | Pr | H | | 69–71 | E-HX |
| 18 | Et | Pr | 4-Cl | | 103–104 | HX |
| 19 | Et | Pr | 4-F | | 85–86 | HX |
| 20 | Et | Pr | 4-OMe | | 89–90 | HX |
| 21 | Me | i-Bu | H | | 100–102 | E-HX |
| 22 | Me | Ph | H | | 145–146 | IP |
| 23 | Me | Ph | 4-Cl | | 150–152 | IP |
| 24 | Me | Ph | 3-Cl | | 149–151 | IP |
| 25 | Me | Ph | 4-F | | 146–148 | IP |
| 26 | Me | Ph | 4-OMe | | 173–174 | IP |
| 27 | Me | Ph | 4-$CF_3$ | | 192–194 | IP |
| 28 | Me | Ph | 4-$NO_2$ | | 199–201 | AC |
| 29 | Me | Ph-4-Cl | H | | 165–166 | IP |
| 30 | Me | Ph-2-Cl | H | | 137–138 | IP |
| 31 | Me | Ph-3-Cl | H | | 129–130 | IP |
| 32 | Me | Ph-4-Cl | 4-Cl | | 170–171 | IP |
| 33 | Me | Ph-4-Cl | 4-F | | 174–175 | IP |
| 34 | Me | Ph-4-Cl | 4-OMe | | 157–158 | IP |
| 35 | Me | Ph-4-F | H | ¼ $H_2O$ | 140–142 | A |
| 36 | Me | Ph-4-F | 4-Cl | | 163–164 | A |
| 37 | Me | Ph-4-Br | H | | 183–184 | A |
| 38 | Me | Ph-4-Br | 4-Cl | | 176–177 | IP |
| 39 | Me | Ph-4-Br | 4-F | | 184–185 | IP |
| 40 | Me | Ph-4-Br | 4-OMe | | 168–169 | IP |
| 41 | Me | Ph-4-OMe | H | | 166–167 | A |
| 42 | Me | Ph-4-OMe | 4-Cl | | 173–174 | A |
| 43 | Me | Ph-4-OMe | 4-F | | 172–173 | IP |
| 44 | Et | Ph | H | | 138–139 | E |
| 45 | Et | Ph | 4-Cl | | 142–143 | IP |
| 46 | Et | Ph | 3-Cl | | 135–137 | IP |
| 47 | Et | Ph | 4-F | | 132–133 | IP |
| 48 | Et | Ph | 4-OMe | | 133–134 | IP |

TABLE 13-continued

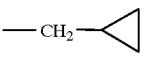

| Ex. | R₁ | R₂ | R₇ | Q | M.p. (°C.) | Solv. for recrystal. |
|---|---|---|---|---|---|---|
| 49 | Et | Ph | 4-CF₃ | | 166–167 | IP |
| 50 | Et | Ph | 4-NO₂ | | 180–182 | AC |
| 51 | Et | Ph-4-Cl | H | | 194–196 | A |
| 52 | Pr | Ph | H | | 148–149 | IP |
| 53 | Pr | Ph | 4-Cl | | 174–175 | A |
| 54 | Pr | Ph | 4-F | | 164–165 | IP |
| 55 | Pr | Ph | 4-OMe | | 125–126 | IP |
| 56 | Pr | Ph-4-Cl | H | | 167–169 | A |
| 57 | Bu | Ph | H | | 134–135 | |
| 58 | —CH₂CH=CH₂ | Ph | H | | 125–126 | IP |
| 59 | —CH₂CH=CH₂ | Ph | 4-Cl | | 151–152 | A |
| 60 | —CH₂CH=CH₂ | Ph | 4-OMe | | 118–119 | IP |
| 61 | 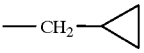 | Ph | H | | 105–106 | E-HX |
| 62 | —CH₂—◁ | Ph | 4-Cl | | 157–158 | A |
| 63 | H | Ph | H | | 155–156 | E |

EXAMPLES 64–68

The corresponding starting compounds are treated in the same manner as in Example 1 to give the following compounds.

(Example 64)
N-Cyclohexyl-N-methyl-2-(5,6-dimethyl-2-phenyl-4-pyrimidinylamino)-acetamide; m.p. 112–114° C. (recrystallized from n-hexane)

(Example 65)
3,5-Dimethyl-1-(5,6-dimethyl-2-phenyl-4-pyrimidinylamino)acetylpiperidine; m.p. 97–98° C. (recrystallized from n-hexane)

(Example 66)
(a) 2,6-Dimethyl-4-(5,6-dimethyl-2-phenyl-4-pyrimidinylamino)acetylmorpholine; m.p. 151–152° C. (recrystallized from isopropanol)
(b) cis-2,6-Dimethyl-4-(5,6-dimethyl-2-phenyl-4-pyrimidinylamino)acetylmorpholine;
The compound obtained in Example 29a is purified by silica gel flash column chromatography (eluent; n-hexane:ethyl acetate=3:1), and the less polar fractions are combined, concentrated under reduced pressure, and recrystallized from isopropanol to give the desired compound, m.p. 162–163° C.
(c) trans-2,6-Dimethyl-4-(5,6-dimethyl-2-phenyl-4-pyrimidinylamino)acetylmorpholine;
The compound obtained in Example 29a is purified by silica gel flash column chromatography (eluent; n-hexane:ethyl acetate=3:1), and the more polar fractions are combined, concentrated under reduced pressure, and recrystallized from a mixture of diethyl ether and n-hexane to give the desired compound, m.p. 112–113° C.

(Example 67)
cis-3,5-Dimethyl-1-(5,6-dimethyl-2-phenyl-5-pyrimidinylamino)acetylpiperazine; m.p. 134–137° C. (recrystallized from a mixture of diethyl ether and n-hexane)

(Example 68)
4-[2-(4-Chlorophenyl)-5,6-dimethyl-4-pyrimidinylamino]acetyl-2,6-dimethylmorpholine; m.p. 212–214° C. (recrystallized from isopropanol)

EXAMPLE 69

Preparation of 3-hydroxy-2-(5,6-dimethyl-2-phenyl-4-pyrimidinylamino)-N,N-dipropylpropanamide:

(1) A mixture of 4-chloro-5,6-dimethyl-2-phenylpyrimidine (1.8 g), 2-amino-3-benzyloxy-N,N-dipropylpropanamide (4.6 g), which is prepared from N-(tert-butoxycarbonyl)-O-benzylserine, and triethylamine (1.7 g) is stirred at 150° C. for 5 hours. The reaction mixture is treated in the same manner as in Example 1 to give 3-benzyloxy-2-(5,6-dimethyl-2-phenyl-4-pyrimidinylamino)-N,N-dipropylpropanamide (3.5 g) as an oily product.

(2) A mixture of the above product (3.4 g), acetic acid (50 ml), water (10 ml), ethanol (10 ml) and 10% palladium-carbon (0.5 g) is stirred at 60° C. for five hours under hydrogen atmosphere, and the reaction mixture is filtered. The filtrate is concentrated under reduced pressure, and the residue is recrystallized from a mixture of diethyl ether and n-hexane to give the desired compound (2.5 g), m.p. 132–133° C.

EXAMPLE 70

Preparation of 2-[methyl-(5,6-dimethyl-2-phenyl-4-pyrimidinyl)amino]-N,N-dipropylacetamide:

The same procedures as Example 1 are repeated except that 2-methylamino-N,N-dipropylacetamide is used instead of 2-amino-N,N-dipropylacetamide, and to the product thus obtained is added hydrogen chloride isopropanol solution. The precipitated crystals are collected by filtration, and washed with diethyl ether to give a hydrochloride 1/10 hydrate of the desired compound, m.p. 162–165° C.

EXAMPLES 71–78

The corresponding starting compounds are treated in the same manner as in Example 1 to give the compounds as listed in Table 14.

TABLE 14

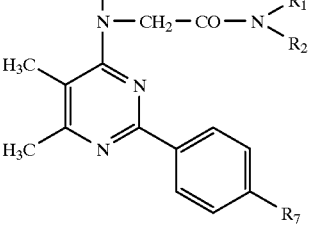

| Ex. | $R_1$ | $R_2$ | $R_4$ | $R_7$ | M.p. (°C.) | Solv. for recrystal. |
|---|---|---|---|---|---|---|
| 71 | Pr | Pr | Et | Cl | 85–86 | HX |
| 72 | Pr | Pr | Et | OMe | 111–112 | HX |
| 73 | Me | Ph | Me | H | 117–119 | IP |
| 74 | Me | Ph | Me | F | 140–141 | IP |
| 75 | Me | Ph | Me | OMe | 151–152 | IP |
| 76 | Me | Ph-4-Cl | Me | H | 114–115 | IP |
| 77 | Me | Ph | Et | H | 107–108 | HX |
| 78 | Me | Ph | Et | Cl | 100–101 | HX |

EXAMPLE 79

Preparation of N-(4-chlorophenyl)-N-methyl-1-(5,6-dimethyl-2-phenyl-4-pyrimidinyl)-2-pyrrolidinecarboxamide:

The same procedures as Example 1 are repeated except that N-(4-chlorophenyl)-N-methyl-2-pyrrolidinecarboxamide is used instead of 2-amino-N,N-dipropylacetamide, and to the product thus obtained is added hydrogen chloride diethyl ether solution. The precipitated crystals are collected by filtration, and washed with diethyl ether to give a hydrochloride of the desired compound, m.p. 119–121° C.

EXAMPLE 80

Preparation of N-(4-chlorophenyl)-N-methyl-1-(5,6-dimethyl-2-phenyl-4-pyrimidinyl)-2-piperidinecarboxamide:

The same procedures as Example 1 are repeated except that N-(4-chlorophenyl)-N-methyl-2-piperidinecarboxamide is used instead of 2-amino-N,N-dipropylacetamide. The product thus obtained is recrystallized from a mixture of diethyl ether and n-hexane to give a 1/10 hydrochloride of the desired compound, m.p. 149–151° C.

EXAMPLE 81

Preparation of 2,3-dihydro-1-(5,6-dimethyl-2-phenyl-4-pyrimidinyl)-N,N-dipropyl-1H-indole-2-carboxamide:

The same procedures as Example 1 are repeated except that 2,3-dihydro-N,N-dipropyl-1H-indole-2-carboxamide is used instead of 2-amino-N,N-dipropylacetamide. The product thus obtained is recrystallized from n-hexane to give a 1/4 hydrate of the desired compound, m.p. 167–168° C.

EXAMPLE 82

Preparation of N-(4-chlorophenyl)-2,3-dihydro-N-methyl-1-(5,6-dimethyl-2-phenyl-4-pyrimidinyl)-1H-indole-2-carboxamide:

The same procedures as Example 1 are repeated except that N-(4-chlorophenyl)-2,3-dihydro-N-methyl-1H-indole-2-carboxamide is used instead of 2-amino-N,N-dipropylacetamide. The product thus obtained is recrystallized from methanol to give a 1/10 hydrochloride.1/4 hydrate of the desired compound, m.p. 236–238° C.

EXAMPLE 83

Preparation of 2-(5-ethyl-6-methyl-2-phenyl-4-pyrimidinylamino)-N,N-dipropylacetamide:

The same procedures as Example 1 are repeated except that 4-chloro-5-ethyl-6-methyl-2-phenylpyrimidine is used instead of 4-chloro-5,6-dimethyl-2-phenylpyrimidine. The product thus obtained is recrystallized from a mixture of diethyl ether and n-hexane to give the desired compound, m.p. 83–84° C.

EXAMPLE 84

Preparation of N-(4-chlorophenyl)-2-(5-ethyl-6-methyl-2-phenyl-4-pyrimidinylamino)-N-methylacetamide:

The same procedures as Example 1 are repeated except that 4-chloro-5-ethyl-6-methyl-2-phenylpyrimidine and 2-amino-N-(4-chlorophenyl)-N-methylacetamide are used instead of 4-chloro-5,6-dimethyl-2-phenylpyrimidine and 2-amino-N,N-dipropylacetamide, respectively. The product thus obtained is recrystallized from isopropanol to give the desired compound, m.p. 142–143° C.

EXAMPLE 85

Preparation of 2-(6-ethyl-5-methyl-2-phenyl-4-pyrimidinylamino)-N,N-dipropylacetamide:

The same procedures as Example 1 are repeated except that 4-chloro-6-ethyl-5-methyl-2-phenylpyrimidine is used instead of 4-chloro-5,6-dimethyl-2-phenylpyrimidine. The product thus obtained is recrystallized from a mixture of diethyl ether and n-hexane to give the desired compound, m.p. 83–84° C.

EXAMPLE 86

Preparation of 2-(6-isopropyl-5-methyl-2-phenyl-4-pyrimidinylamino)-N,N-dipropylacetamide:

The same procedures as Example 1 are repeated except that 4-chloro-6-isopropyl-5-methyl-2-phenylpyrimidine is used instead of 4-chloro-5,6-dimethyl-2-phenylpyrimidine. The product thus obtained is recrystallized from a mixture of diethyl ether and n-hexane to give the desired compound, m.p. 98–99° C.

EXAMPLE 87

Preparation of 2-(6-methyl-2-phenyl-4-pyrimidinylamino)-N,N-dipropylacetamide:

The same procedures as Example 1 are repeated except that 4-chloro-6-methyl-2-phenylpyrimidine is used instead of 4-chloro-5,6-dimethyl-2-phenylpyrimidine. The product thus obtained is recrystallized from diethyl ether to give the desired compound, m.p. 107–108° C.

EXAMPLE 88

Preparation of 2-(6-methyl-2-phenyl-4-pyrimidinylamino)-N-methyl-N-phenylacetamide:

The same procedures as Example 1 are repeated except that 4-chloro-6-methyl-2-phenylpyrimidine and 2-amino-N-methyl-N-phenylacetamide are used instead of 4-chloro-5,6-dimethyl-2-phenylpyrimidine and 2-amino-N,N-dipropylacetamide, respectively. The product thus obtained is recrystallized from isopropanol to give the desired compound, m.p. 134–136° C.

EXAMPLE 89

Preparation of 2-(5-chloro-6-methyl-2-phenyl-4-pyrimidinylamino)-N-methyl-N-phenylacetamide:

A mixture of 2-(6-methyl-2-phenyl-4-pyrimidinylamino)-N-methyl-N-phenylacetamide (1.0 g) obtained in Example 88, N-chlorosuccinimide (0.44 g) and acetic acid (15 ml) is heated with stirring at 90° C. for three hours, and the reaction mixture is concentrated under reduced pressure. To the residue is added ice-water (30 ml) with stirring, and the precipitates are collected by filtration, washed with water, and recrystallized from isopropanol to give the desired compound (1.1 g), m.p. 154–155° C.

EXAMPLE 90

Preparation of 2-(5-bromo-6-methyl-2-phenyl-4-pyrimidinylamino)-N-methyl-N-phenylacetamide:

The same procedures as Example 89 are repeated except that N-bromosuccinimide is used instead of N-chlorosuccinimide. The product thus obtained is recrystallized from isopropanol to give the desired compound, m.p. 160–162° C.

EXAMPLE 91

Preparation of 2-(2-phenyl-6-trifluoromethyl-4-pyrimidinylamino)-N,N-dipropyl-acetamide:

The same procedures as Example 1 are repeated except that 4-chloro-6-trifluoromethyl-2-phenylpyrimidine is used instead of 4-chloro-5,6-dimethyl-2-phenylpyrimidine. The product thus obtained is recrystallized from isopropanol to give the desired compound, m.p. 128–130° C.

EXAMPLE 92

Preparation of 2-(5-chloro-2-phenyl-6-trifluoromethyl-4-pyrimidinylamino)-N,N-dipropylacetamide:

The same procedures as Example 89 are repeated except that 2-(2-phenyl-6-trifluoromethyl-4-pyrimidinylamino)-N-methyl-N-phenylacetamide is used instead of 2-(6-methyl-2-phenyl-4-pyrimidinylamino)-N-methyl-N-phenylacetamide. The product thus obtained is recrystallized from isopropanol to give the desired compound, m.p. 115–117° C.

EXAMPLES 93–99

The corresponding starting compounds are treated in the same manner as in Example 1 to give the compounds as listed in Table 15.

TABLE 15

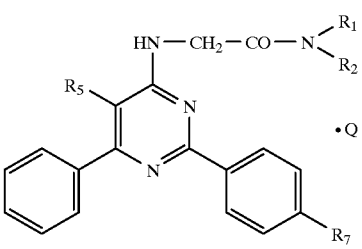

| Ex. | $R_1$ | $R_2$ | $R_5$ | $R_7$ | Q | M.p. (°C.) | Solv. for recrystal. |
|---|---|---|---|---|---|---|---|
| 93 | Pr | Pr | H | H | | 102–103 | E-HX |
| 94 | Pr | Pr | H | Cl | | 146–148 | IP |
| 95 | Me | Ph | H | Cl | 1/10 HCl | 180–181 | A |
| 96 | Me | Ph-4-Cl | H | H | 1/4 $H_2O$ | 157–158 | IP |
| 97 | Pr | Pr | Me | H | | 139–140 | IP |
| 98 | Pr | Pr | Me | Cl | | 129–130 | IP |
| 99 | Me | Ph | Me | H | | 146–147 | IP |

EXAMPLE 100

Preparation of 3,5-dimethyl-1-(2,6-diphenyl-4-pyrimidinylamino)acetylpiperidine:

The same procedures as Example 1 are repeated except that 4-chloro-2,6-diphenylpyrimidine and 1-aminoacetyl-3,5-dimethylpiperidine are used instead of 4chloro-5,6-dimethyl-2-phenylpyrimidine and 2-amino-N,N-dipropylacetamide, respectively. The product thus obtained is recrystallized from isopropanol to give the desired compound, m.p. 134–135° C.

EXAMPLE 101

Preparation of 2-(2-phenyl-4-pyrimidinylamino)-N,N-dipropylacetamide:

The same procedures as Example 1 are repeated except that 4-chloro-2-phenylpyrimidine, which is prepared according to the method disclosed in Rec. Trav. Chim. Pays-Bas, 86, 15 (1967), is used instead of 4-chloro-5,6-dimethyl-2-phenylpyrimidine. The product thus obtained is recrystallized from diethyl ether to give the desired compound, m.p. 74–75° C.

EXAMPLE 102

Preparation of 2-(5,6,7,8-tetrahydro-2-phenyl-4-quinazolinylamino)-N,N-dipropylacetamide:

A mixture of 4-chloro-5,6,7,8-tetrahydro-2-phenylquinazoline (1.0 g), 2-amino-N,N-dipropylacetamide (0.78 g) and triethylamine (0.5 g) is refluxed with stirring at 150° C. for three hours. To the reaction mixture are added water and chloroform, and the chloroform layer is separated, dried over anhydrous sodium sulfate, and concentrated under reduced pressure. The residue is purified by silica gel column chromatography (eluent; chloroform), and recrystallized from a mixture of diethyl ether and n-hexane to give the desired compound (1.3 g), m.p. 87–88° C.

EXAMPLES 103–112

The corresponding starting compounds are treated in the same manner as in Example 102 to give the compounds as listed in Table 16.

TABLE 16

| Ex. | R₁ | R₂ | R₄ | R₇ | Q | M.p. (°C.) | Solv. for recrystal. |
|---|---|---|---|---|---|---|---|
| 103 | Pr | Pr | H | F | | 88–89 | HX |
| 104 | Pr | Pr | H | Cl | | 98–99 | E-HX |
| 105 | Bu | Bu | H | H | | 71–72 | HX |
| 106 | Bu | Bu | H | F | | 65–66 | HX |
| 107 | Bu | Bu | H | Cl | | 83–84 | HX |
| 108 | Me | Ph-4-Cl | H | H | | 225–227 | M |
| 109 | Me | Ph-4-Cl | H | Cl | | 177–178 | IP |
| 110 | Pr | Pr | Me | H | HCl, ¾ H₂O | 154–156 | IP |
| 111 | Me | Ph-4-Cl | Me | H | ⅒ HCl | 176–177 | IP |
| 112 | Me | Ph-4-Cl | Me | F | | 139–140 | IP |

EXAMPLES 113–117

The corresponding starting compounds are treated in the same manner as in Example 102 to give the compounds as listed in Table 17.

TABLE 17

| Ex. | A | R₇ | M.p. (°C.) | Solv. for recrystal. |
|---|---|---|---|---|
| 113 | O | H | 164–165 | IP |
| 114 | O | F | 212–214 | A |
| 115 | O | Cl | 225–227 | A |
| 116 | NH | H | 178–179 | IP |
| 117 | NH | F | 195–197 | IP |

EXAMPLE 118

Preparation of 3-hydroxy-2-(5,6,7,8-tetrahydro-2-phenyl-4-quinazolinylamino)-N,N-dipropylpropanamide:

(1) The same procedures as Example 102 are repeated except that 2-amino-3-benzyloxy-N,N-dipropylpropanamide (4.1 g) is used instead of 2-amino-N,N-dipropylacetamide to give 3-benzyloxy-2-(5,6,7,8-tetrahydro-2-phenyl-4-quinazolinylamino)-N,N-dipropylpropanamide (3.4 g) as an oily product.

(2) A mixture of the above product (3.0 g), acetic acid (100 ml) and 10% palladium-carbon (1.0 g) is stirred at 60° C. for six hours under hydrogen atmosphere, and the reaction mixture is filtered. The filtrate is concentrated under reduced pressure and recrystallized from diethyl ether to give the desired compound (2.0 g), m.p. 119–120° C.

EXAMPLES 119–120

Instead of 2-amino-N,N-dipropylacetamide, the corresponding starting compounds are treated in the same manner as in Example 102 to give the following compounds.
(Example 119)
1-(5,6,7,8-Tetrahydro-2-phenyl-4-quinazolinyl)-N,N-dipropyl-2-pyrrolidinecarboxamide; m.p. 123–124° C. (recrystallized from diethyl ether)
(Example 120)
N-(4-Chlorophenyl)-1-(5,6,7,8-tetrahydro-2-phenyl-4-quinazolinyl)-N-methyl-2-pyrrolidinecarboxamide ¼ hydrate; m.p. 80–82° C. (recrystallized from n-hexane)

EXAMPLE 121

Preparation of 2-(5-nitro-2-phenyl-4-pyrimidinylamino)-N,N-dipropylacetamide:

A mixture of 4-chloro-5-nitro-2-phenylpyrimidine (6.0 g), 2-amino-N,N-dipropylacetamide (6.0 g), triethylamine (5.2 g) and isopropanol (70 ml) is refluxed for six hours. The reaction mixture is concentrated under reduced pressure, and to the residue are added chloroform and water. The chloroform layer is collected, dried over anhydrous sodium sulfate, and concentrated under reduced pressure. The residue is purified by silica gel column chromatography (eluent; chloroform), and recrystallized from ethanol to give the desired compound (8.8 g), m.p. 142–143° C.

EXAMPLE 122

Preparation of 2-(5-amino-2-phenyl-4-pyrimidinylamino)-N,N-dipropylacetamide;

A mixture of 2-(5-nitro-2-phenyl-4-pyrimidinylamino)-N,N-dipropylacetamide (1.9 g) obtained in Example 121, ethanol (60 ml) and 10% palladiumcarbon (0.2 g) is stirred at room temperature for three hours under hydrogen atmosphere, and the reaction mixture is filtered. The filtrate is concentrated under reduced pressure, and recrystallized from diethyl ether to give the desired compound (1.5 g), m.p. 120–122° C.

EXAMPLE 123

Preparation of N-methyl-2-(5-nitro-2-phenyl-4-pyrimidinylamino)-N-phenylacetamide:

The same procedures as Example 121 are repeated except that 2-amino-N-methyl-N-phenylacetamide (7.3 g) is used instead of 2-amino-N,N-dipropylacetamide. The product thus obtained is recrystallized from ethanol to give the desired compound (10.1 g), m.p. 194–196° C.

EXAMPLE 124

Preparation of 2-(5-amino-2-phenyl-4-pyrimidinylamino)-N-methyl-N-phenylacetamide:

2-(5-Nitro-2-phenyl-4-pyrimidinylamino)-N-methyl-N-phenylacetamide (5.5 g) obtained in Example 123 is treated in the same manner as in Example 122, and the product thus obtained is recrystallized from ethanol to give a ¼ hydrate of the desired compound (4.8 g), m.p. 183–184° C.

EXAMPLE 125
Preparation of 2-(5-acetylamino-2-phenyl-4-pyrimidinylamino)-N-methyl-N-phenylacetamide:

A mixture of 2-(5-amino-2-phenyl-4-pyrimidinylamino)-N-methyl-N-phenylacetamide (3.6 g) obtained in Example 124, acetic anhydride (10 ml) and pyridine (7 ml) is stirred at room temperature for four hours. To the reaction mixture is added chloroform, and the mixture is washed with 1N hydrochloric acid, then washed with a saturated aqueous sodium hydrogen carbonate solution. The chloroform layer is collected, dried over anhydrous sodium sulfate, and concentrated under reduced pressure. The residue is purified by silica gel column chromatography (eluent; chloroform), and recrystallized from ethanol to give the desired compound (4.0 g), m.p. 200–201° C.

EXAMPLE 126
Preparation of 2-(5-ethoxycarbonyl-2-phenyl-4-pyrimidinylamino)-N,N-dipropylacetamide:

The same procedures as Example 1 are repeated except that 4-chloro-5-ethoxycarbonyl-2-phenylpyrimidine (6.0 g) is used instead of 4-chloro-5,6-dimethyl-2-phenylpyrimidine. The product thus obtained is recrystallized from n-hexane to give the desired compound, m.p. 45–46° C.

EXAMPLE 127
Preparation of 2-(5-hydroxymethyl-2-phenyl-4-pyrimidinylamino)-N,N-dipropylacetamide:

To a mixture of 2-(5-ethoxycarbonyl-2-phenyl-4-pyrimidinylamino)-N,N-dipropylacetamide (3.0 g) obtained in Example 126, sodium borohydride (0.6 g), lithium chloride (0.7 g) and tetrahydrofuran (20 ml) is added dropwise anhydrous ethanol (30 ml) at 0 to 5° C. The reaction mixture is stirred at room temperature for five hours, and the pH value thereof is adjusted to pH 5 with 1N hydrochloric acid, and concentrated under reduced pressure. To the residue are added a brine and chloroform, and the chloroform layer is collected, dried over anhydrous sodium sulfate, and concentrated under reduced pressure. The residue is purified by silica gel column chromatography (eluent; chloroform), and recrystallized from isopropanol to give the desired compound (2.0 g), m.p. 167–168° C.

EXAMPLE 128
Preparation of 2-[2-(4-fluorophenyl)-5,6,7,8-tetrahydro-4-quinazolinyloxy]-N,N-dipropylacetamide:

To a mixture of 2-hydroxy-N,N-dipropylacetamide (1.8 g) and dimethylformamide (20 ml) is added sodium hydride (about 60% oily, 0.5 g) at 0 to 5° C., and the mixture is stirred at 0° C. for one hour. To the reaction mixture is added 4-chloro-2-(4-fluorophenyl)-5,6,7,8-tetrahydroquinazoline (2.0 g) at the same temperature, and the mixture is stirred at room temperature for four hours. To the mixture are added chloroform and ice-water, and the chloroform layer is collected, washed with water, dried over anhydrous sodium sulfate, and concentrated under reduced pressure. The residue is purified by silica gel column chromatography (eluent; chloroform), and recrystallized from a mixture of diethyl ether and n-hexane to give the desired compound (2.2 g), m.p. 95–96° C.

EXAMPLES 129–135

The corresponding starting compounds are treated in the same manner as in Example 128 to give the compounds as listed in Table 18.

TABLE 18

| Ex. | $R_1$ | $R_2$ | $R_7$ | $R_8$ | M.p. (°C.) | Solv. for recrystal. |
|---|---|---|---|---|---|---|
| 129 | Pr | Pr | 2-Cl | H | 75–76 | HX |
| 130 | Pr | Pr | 3-Cl | H | 100–101 | HX |
| 131 | Pr | Pr | 4-Cl | H | 119–120 | IP |
| 132 | Pr | Pr | 2-F | 4-F | 93–94 | HX |
| 133 | Bu | Bu | H | H | 84–85 | HX |
| 134 | Bu | Bu | 4-F | H | 90–91 | HX |
| 135 | Bu | Bu | 4-Cl | H | 105–106 | IP |

EXAMPLE 136
Preparation of 2-(5,6-dimethyl-2-phenyl-4-pyrimidinyloxy)-N,N-dipropylacetamide:

To a mixture of 5,6-dimethyl-2-phenyl-4-(3H)-pyrimidinone (1.5 g) and dimethylformamide (20 ml) is added sodium hydride (about 60% oily, 0.3 g) at 0–5° C., the mixture is stirred at 0° C. for one hour. To the mixture is added 2-dipropylacetamide (1.67 g) at the same temperature, and the mixture is stirred at room temperature for two hours. To the reaction mixture are added chloroform and ice-water, and the chloroform layer is collected, washed with water, dried over anhydrous sodium sulfate, and concentrated under reduced pressure. The residue is purified by silica gel column chromatography (eluent; chloroform), and recrystallized from n-hexane to give the desired compound (2.2 g), m.p. 88–89° C.

EXAMPLE 137–163

The corresponding starting compounds are treated in the same manner as in Example 136 to give the compounds as listed in Table 19.

TABLE 19

[Structure: pyrimidine with O-CH2-CO-N(R1)(R2) at 4-position, R5 at 5, R6 at 6, 2-phenyl bearing R7; ·Q]

| Ex. | R$_5$ | R$_6$ | R$_1$ | R$_2$ | R$_7$ | Q | M.p. (°C.) | Solve. for recrystal. |
|---|---|---|---|---|---|---|---|---|
| 137 | Me | Me | Pr | Pr | 4-Cl | | 128–130 | E-HX |
| 138 | Me | Me | Pr | Pr | 4-F | | 131–133 | A |
| 139 | Me | Me | Pr | Pr | 4-OMe | | 87–88 | HX |
| 140 | Me | Me | Pr | Pr | 3-Cl | | 82–84 | E-HX |
| 141 | Me | Me | Pr | Pr | 4-CF$_3$ | | 109–111 | HX |
| 142 | Me | Me | Pr | Pr | 4-NO$_2$ | | 157–159 | M |
| 143 | Me | Me | Me | Ph | H | | 138–139 | IP |
| 144 | Me | Me | Me | Ph | 4-Cl | | 159–161 | A |
| 145 | Me | Me | Me | Ph | 3-Cl | | 170–173 | IP |
| 146 | Me | Me | Me | Ph | 4-OMe | | 157–159 | IP |
| 147 | Me | Me | Me | Ph | 4-CF$_3$ | | 159–161 | IP |
| 148 | Me | Me | Me | Ph | 4-NO$_2$ | | 179–181 | AC |
| 149 | Me | Me | Me | Ph-4-Cl | H | | 168–170 | IP |
| 150 | Me | Me | Me | Ph-4-Cl | 4-OMe | | 142–143 | A |
| 151 | Me | Me | Et | Ph | H | | 130–132 | IP |
| 152 | Me | Me | Et | Ph | 4-Cl | | 170–171 | A |
| 153 | Me | Me | Et | Ph | 3-Cl | | 151–153 | IP |
| 154 | Me | Me | Et | Ph | 4-F | | 156–158 | IP |
| 155 | Me | Me | Et | Ph | 4-CF$_3$ | | 148–150 | IP |
| 156 | Et | Me | Me | Ph-4-Cl | H | | 100–101 | E-HX |
| 157 | Me | Et | Pr | Pr | H | | 62–63 | HX |
| 158 | H | Ph | Pr | Pr | H | | 82–83 | E |
| 159 | Me | Ph | Pr | Pr | H | | 78–79 | HX |
| 160 | H | CF$_3$ | Pr | Pr | H | | 109–110 | IP |
| 161 | —(CH$_2$)$_4$— | | Pr | Pr | H | | 92–93 | E-HX |
| 162 | —(CH$_2$)$_4$— | | Me | Ph-4-Cl | H | | 140–141 | IP |
| 163 | —(CH$_2$)$_4$— | | Me | Ph-4-Cl | 4-Cl | ¼ H$_2$O | 200–202 | A |

EXAMPLE 164
Preparation of N-ethyl-2-[5,6-dimethyl-2-(4-nitrophenyl)-4-pyrimidinyloxy]-N-phenylacetamide:

The same procedures as Example 136 are repeated except that 5,6-dimetyl-2-(4-nitrophenyl)-4-(3H)-pyrimidinone and 2-bromo-N-ethyl-N-phenylacetamide are used instead of 5,6-dimethyl-2-phenyl-4-(3H)-pyrimidinone and 2-bromo-N,N-dipropylacetamide, respectively. The product thus obtained is recrystallized from acetonitrile to give the desired compound, m.p. 89–190° C.

EXAMPLE 165
Preparation of 2-[2-(4-aminophenyl)-5,6-dimethyl-4-pyrimidinyloxy]-N-ethyl-N-phenylacetamide:

A mixture of 2-[5,6-dimethyl-2-(4-nitrophenyl)-4-pyrimidinyloxy]-N-ethyl-N-phenylacetamide (2.3 g) obtained in Example 164, 5% palladiumcarbon (0.4 g), ethanol (30 ml) and chloroform (10 ml) is stirred at room temperature for three hours under hydrogen atmosphere, and the reaction mixture is filtered. The filtrate is concentrated under reduced pressure, and recrystallized from acetonitrile to give a ¹/₁₀ hydrate of the desired compound (2.1 g), m.p. 183–185° C.

EXAMPLE 166
Preparation of 2-(6-methyl-2-phenyl-4-pyrimidinyloxy)-N,N-dipropylacetamide:

The same procedures as Example 136 are repeated except that 6-methyl-2-phenyl-4-(3H)-pyrimidinone is used instead of 5,6-dimethyl-2-phenyl-4-(3H)-pyrimidinone. The product thus obtained is recrystallized from n-hexane to give the desired compound, m.p. 68–69° C.

EXAMPLE 167
Preparation of 2-(5-chloro-6-methyl-2-phenyl-4-pyrimidinyloxy)-N,N-dipropylacetamide:

2-(6-Methyl-2-phenyl-4-pyrimidinyloxy)-N,N-dipropylacetamide obtained in Example 166 is treated in the same manner as in Example 89, and the product is recrystallized from isopropanol to give the desired compound, m.p. 90–91° C.

EXAMPLE 168
Preparation of 2-(5-bromo-6-methyl-2-phenyl-4-pyrimidinyloxy)-N,N-dipropylacetamide:

2-(6-Methyl-2-phenyl-4-pyrimidinyloxy)-N,N-dipropylacetamide obtained in Example 166 is treated in the same manner as in Example 90, and the product is recrystallized from isopropanol to give the desired compound, m.p. 107–108° C.

EXAMPLE 169
Preparation of 2-(5,6,7,8-tetrahydro-2-phenyl-4-quinazolinyloxy)-N,N-dipropylpropanamide:

The same procedures as Example 136 are repeated except that 5,6,7,8-tetrahydro-2-phenyl-4-(3H)-quinazolinone and 2-bromo-N,N-dipropylpropanamide are used instead of 5,6-dimethyl-2-phenyl-4-(3H)-pyrimidinone and 2-bromo-N,N- dipropylacetamide, respectively. The product thus obtained is recrystallized from n-hexane to give the desired compound, m.p. 73–74° C.

EXAMPLE 170

Preparation of 3,5-dimethyl-1-(5,6-dimethyl-2-phenyl-4-pyrimidinyloxy)acetylpiperidine:

To a mixture of 2-(5,6-dimethyl-2-phenyl-4-pyrimidinyloxy)acetic acid (1.2 g), 3,5-dimethylpiperidine (0.7 g), benzotriazol-1-yloxy-tris(dimethylamino) phosphonium • hexafluorophosphate (BOP reagent; 2.26 g) and dimethylformamide (20 ml) is added triethylamine (0.52 g) at 0–5° C., and the mixture is stirred at room temperature for six hours. To the reaction mixture are added chloroform and ice-water, and the chloroform layer is collected, washed with water, dried over anhydrous sodium sulfate, and concentrated under reduced pressure. The residue is purified by silica gel column chromatography (eluent; chloroform), and recrystallized from n-hexane to give the desired compound (1.4 g), m.p. 100–101° C.

EXAMPLES 171–173

Instead of 3,5-dimethylpiperidine, the corresponding starting compounds are treated in the same manner as in Example 170 to give the following compounds.
(Example 171)
2,6-Dimethyl-4-(5,6-dimethyl-2-phenyl-4-pyrimidinyloxy)acetylmorpholine; m.p. 123–124° C. (recrystallized from isopropanol)
(Example 172)
3,5-Dimethyl-1-(5,6-dimethyl-2-phenyl-4-pyrimidinyloxy)acetylpiperazine • ¼ hydrate; m.p. 107–110° C. (recrystallized from a mixture of diethyleter and n-hexane)
(Example 173)
2,3-Dihydro-1-(5,6-dimethyl-2-phenyl-4-pyrimidinyloxy)acetyl-1H-indole; m.p. 210–212° C. (recrystallized from acetonitrile)

EXAMPLES 174–188

The corresponding starting compounds are treated in the same manner as in Example 170 to give the compounds as listed in Table 20.

TABLE 20

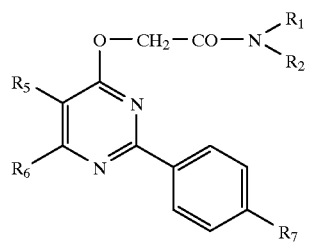

| Ex. | $R_5$ | $R_6$ | $R_1$ | $R_2$ | $R_7$ | M.p. (°C.) | Solv. for recrystal. |
|---|---|---|---|---|---|---|---|
| 174 | Me | Me | Me | Me | H | 128–129 | IP |
| 175 | Me | Me | Et | Et | H | 88–90 | E-HX |
| 176 | Me | Me | Et | Et | Cl | 148–149 | IP |
| 177 | Me | Me | Bu | Bu | H | 99–100 | E-HX |
| 178 | Me | Me | Pr | Ph | H | 151–152 | IP |
| 179 | —(CH$_2$)$_4$— | | Et | Et | H | 100–101 | E-HX |
| 180 | —(CH$_2$)$_4$— | | Me | Ph | H | 135–137 | IP |
| 181 | —(CH$_2$)$_4$— | | Me | Ph | Cl | 148–150 | IP |

TABLE 20-continued

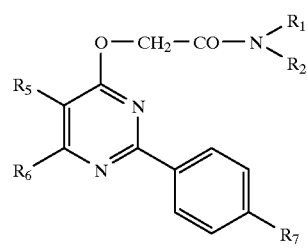

| Ex. | $R_5$ | $R_6$ | $R_1$ | $R_2$ | $R_7$ | M.p. (°C.) | Solv. for recrystal. |
|---|---|---|---|---|---|---|---|
| 182 | —(CH$_2$)$_4$— | | Pr | Ph | H | 158–160 | IP |
| 183 | —(CH$_2$)$_4$— | | H | Ph-4-F | H | 178–179 | M |
| 184 | —(CH$_2$)$_4$— | | Me | Ph-4-F | H | 164–165 | IP |
| 185 | —(CH$_2$)$_4$— | | H | Ph-4-Cl | H | 179–180 | A |
| 186 | —(CH$_2$)$_4$— | | Me | Ph-2-Cl | H | 165–166 | A |
| 187 | —(CH$_2$)$_4$— | | Me | Ph-3-Cl | H | 180–182 | A |
| 188 | —(CH$_2$)$_4$— | | Me | CH$_2$Ph | H | 91–92 | E |

EXAMPLE 189

Preparation of 2-(5,6-dimethyl-2-phenyl-4-pyrimidinyloxy)-N-phenylacetamide:

The same procedures as Example 170 are repeated except that aniline is used instead of 3,5-dimethylpiperidine. The product thus obtained is recrystallized from isopropanol to give the desired compound, m.p. 212–213° C.

EXAMPLE 190

Preparation of N-cyclopropylmethyl-2-(5,6-dimethyl-2-phenyl-4-pyrimidinyloxy)-N-phenylacetamide:

To a mixture of 2-(5,6-dimethyl-2-phenyl-4-pyrimidinyloxy)-N-phenylacetamide (1.5 g) obtained in Example 189 and dimethylformamide (30 ml) is added sodium hydride (about 60% oily, 0.2 g) at 0–5° C., and the mixture is stirred at 0° C. for one hour. To the mixture is added cyclopropylmethyl bromide (0.67 g) at the same temperature, and the mixture is stirred at room temperature for two hours. To the reaction solution are added chloroform and ice-water, and the chloroform layer is collected, washed with water, and dried over anhydrous sodium sulfate. The chloroform layer is concentrated under reduced pressure, and the residue is purified by silica gel column chromatography (eluent; chloroform), and recrystallized from isopropanol to give the desired compound (1.56 g), m.p. 119–121° C.

EXAMPLE 191

Preparation of N-allyl-2-(5,6-dimethyl-2-phenyl-4-pyrimidinyloxy)-N-phenylacetamide:

The same procedures as Example 190 are repeated except that allyl bromide is used instead of propylmethyl bromide. The product thus obtained is recrystallized from isopropanol to give the desired compound, m.p. 129–131 ° C.

EXAMPLES 192–196

The corresponding starting compounds are treated in the same manner as in Example 170 to give the following compounds.
(Example 192)
1-(5,6,7,8-Tetrahydro-2-phenyl-4-quinazolinyloxy)acetyl-3,5-dimethylpiperidine; m.p. 134–135° C. (recrystallized from diethyl ether)
(Example 193)

51

4-(5,6,7,8-Tetrahydro-2-phenyl-4-quinazolinyloxy) acetyl-2,6-dimethylmorpholine; m.p. 161–163° C. (recrystallized from isopropanol)

(Example 194)

1-(5,6,7,8-Tetrahydro-2-phenyl-4-quinazolinyloxy) acetyl-cis-3,5-dimethylpiperazine ¼ hydrate; m.p. 150–151° C. (recrystallized from diethyl ether)

(Example 195)

4-[2-(4-Chlorophenyl)-5,6,7,8-tetrahydro-4-quinazolinyloxy] acetyl-2,6-dimethylmorpholine; m.p. 171–173° C. (recrystallized from isopropanol)

(Example 196)

1-[2-(4-Chlorophenyl)-5,6,7,8-tetrahydro-4-quinazolinyloxy]acetyl-cis-3,5-dimethylpiperazine • 9/10 hydrochloride; m.p. 265–268° C. (recrystallized from ethanol)

EXAMPLE 197

Preparation of cis-3,5-dimethyl-1-[(5,6-dimethyl-2-phenyl-4-pyrimidinyl)-2-pyrrolidinylcarbonyl]piperazine:

(1) The same procedures as Example 1 are repeated except that proline benzyl ester hydrochloride (4.0 g) is used instead of 2-amino-N,N-dipropylacetamide. The product thus obtained is recrystallized from isopropanol to give 1-(5,6-dimethyl-2-phenyl-4-pyrimidinyl)-2-pyrrolidinecarboxylic acid (4.0 g), m.p. 90–92° C.

(2) A mixture of the above product (3.8 g), ethanol (100 ml) and 10% palladium-carbon (1.0 g) is stirred at room temperature for 8 hours under hydrogen atmosphere, and the mixture is filtered. The filtrate is concentrated under reduced pressure, and recrystallized from isopropanol to give N-(5,6-dimethyl-2-phenyl-4-pyrimidinyl)proline (2.5 g), m.p. 228–231 ° C.

(3) To a mixture of the above product (1.2 g), cis-3,5-dimethylpiperazine (0.6 g), BOP reagent (1.97 g) and dimethylformamide (30 ml) is added triethylamine (0.52 g) at 0–5° C., and the mixture is stirred at room temperature for five hours. To the reaction mixture are added chloroform and ice-water, and the chloroform layer is collected, washed with water, dried over anhydrous sodium sulfate, and concentrated under reduced pressure. The residue is purified by silica gel column chromatography (eluent; chloroform), and recrystallized from diethyl ether to give a ½ hydrate of the desired compound (1.4 g), m.p. 160–162° C.

EXAMPLES 198–204

The corresponding starting compounds are treated in the same manner as in Example 1 to give the compounds as listed in Table 21.

52

TABLE 21

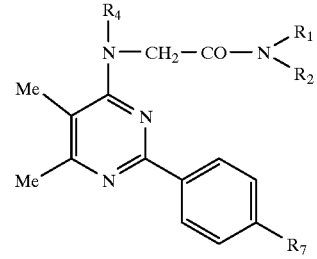

| Ex. | $R_1$ | $R_2$ | $R_4$ | $R_7$ | M.p. (°C.) | Solv. for recrystal. |
|---|---|---|---|---|---|---|
| 198 | Et | Et | Me | Cl | 131–132 | IP |
| 199 | Pr | Pr | Me | Cl | 84–86 | HX |
| 200* | Me | Ph | Me | Cl | 139–140 | IP |
| 201 | Et | Ph | Me | Cl | 102–103 | HX |
| 202 | Pr | Ph | Me | Cl | 103–104 | HX |
| 203 | —CH$_2$CH═CH$_2$ | Ph | Me | Cl | 107–108 | HX |
| 204 | H | Ph | H | Cl | 205–206 | A |

*¼ Hydrate

EXAMPLE 205

Preparation of 1-[2-(4-chlorophenyl)-5,6-dimethyl-4-pyrimidinyl]-N-(4-chlorophenyl)-N-methyl-2-pyrrolidinecarboxamide:

The corresponding starting compounds are treated in the same manner as in Example 1, and the product thus obtained is recrystallized from isopropanol to give the title compound, m.p. 131–133° C.

Preparation 1: Preparation of tablets:

| | |
|---|---|
| 2-[2-(4-Chlorophenyl)-5,6-dimethyl-4-pyrimidinyl-amino]-N-methyl-N-phenylacetamide | 1 g |
| Lactose | 84 g |
| Corn starch | 30 g |
| Crystalline cellulose | 25 g |
| Hydroxypropyl cellulose | 3 g |
| Light anhydrous silicic acid | 0.7 g |
| Magnesium stearate | 1.3 g |

The above components are mixed and kneaded in a conventional manner, and the mixture is granulated, and the resultants are further tabletted to give 1,000 tablets (each 145 mg).

Preparation 2: Preparation of tablets

| | |
|---|---|
| 2-[5,6-Dimethyl-2-(4-trifluoromethylphenyl)-4-pyrimidinylamino]-N,N-dipropylacetamide | 25 g |
| Lactose | 70 g |
| Corn starch | 20 g |
| Crystalline cellulose | 25 g |
| Hydroxypropyl cellulose | 3 g |
| Light anhydrous silicic acid | 0.7 g |
| Magnesium stearate | 1.3 g |

The above components are mixed and kneaded in a conventional manner, and the mixture is granulated, and the resultants are further tabletted to give 1,000 tablets (each 145 mg).

Preparation 3: Preparation of capsules

| | |
|---|---|
| 2-[2-(4-Chlorophenyl)-5,6-dimethyl-4-pyrimidinyl-amino]-N,N-dipropylacetamide | 2 g |
| Lactose | 165 g |
| Corn starch | 25 g |
| Hydroxypropyl cellulose | 3.5 g |
| Light anhydrous silicic acid | 1.8 g |
| Magnesium stearate | 2.7 g |

The above components are mixed and kneaded in a conventional manner, and the mixture is granulated, and each 200 mg of the resultant is packed into a capsule to give 1,000 capsules.

Preparation 4: Preparation of powder

| | |
|---|---|
| N-(4-Chlorophenyl)-N-methyl-2-(5,6-dimethyl-2-phenyl-4-pyrimidinylamino)acetamide | 10 g |
| Lactose | 960 g |
| Hydroxypropyl cellulose | 25 g |
| Light anhydrous silicic acid | 5 g |

The above components are mixed to give powder preparation.

Preparation 5: Preparation of injection preparation

| | |
|---|---|
| 2-[2-(4-Chlorophenyl)-5,6-dimethyl-4-pyrimidinyl-amino]-N-methyl-N-phenylacetamide | 10 g |
| Ethanol | 200 g |
| HCO-60 | 2 g |
| Citric acid | 10 g |
| Sorbitol | 50 g |
| Sodium hydroxide | q.s. |
| Distilled water for injection | q.s |
| Totally | 2000 ml |

2-[2-(4-Chlorophenyl)-5,6-dimethyl-4-pyrimidinylamino]-N-methyl-N-phenylacetamide is dissolved in a mixture of ethanol and HCO-60, and thereto is added a suitable amount of distilled water for injection, and further thereto are added citric acid and sorbitol. The pH value of the mixture is adjusted to pH 4.5 with sodium hydroxide, and the total amount of the mixture is controlled with addition of distilled water for injection. The solution thus obtained is filtered on a membrane filter (0.22 μm), and the filtrate is put into ampules (capacity; 2 ml), and the ampules are sterilized at 121° C. for 20 minutes.

INDUSTRIAL APPLICABILITY

As explained above, the present compounds of the formula (I) or a pharmaceutically acceptable acid addition salt thereof show a selective and remarkable affinity for the peripheral-type $BZ\omega_3$-receptor as well as show excellent pharmacological activities such as anxiolytic activity, anti-epileptic activity, etc. in animal tests, and hence, they are useful in the prophylaxis or treatment of central nervous disorders such as anxiety-related diseases (neurosis, somatoform disorders, other anxiety disorders), depression, epilepsy, etc., or circulatory organs disorders such as angina pectoris, hypertension, etc. Besides, the present compounds of the formula (I) and a pharmaceutically acceptable acid addition salt thereof can be expected to be useful in the prophylaxis or treatment of immuno neurological disorders such as multiple sclerosis, and immuno inflammatory diseases such as rheumatoid arthritis.

We claim:

1. An acetamide derivative of the formula (I):

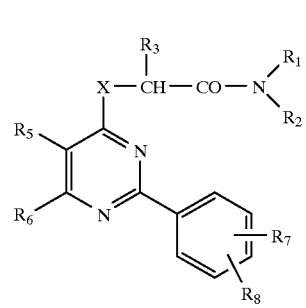

(I)

wherein X is —O— or —$NR_4$—, $R_1$ is a hydrogen atom, a $C_1$–$C_5$ alkyl group, a $C_3$–$C_6$ alkenyl group or a $C_3$–$C_8$ cycloalkyl-$C_1$–$C_4$ alkyl group, $R_2$ is a $C_1$–$C_6$ alkyl group, a $C_3$–$C_8$ cycloalkyl group, a phenyl group which may optionally be substituted by one or two groups selected from a halogen atom, a $C_1$–$C_3$ alkyl group, a $C_1$–$C_3$ alkoxy group, a trifluoromethyl group, an amino group, a mono- or di-$C_1$–$C_3$ alkylamino group, a cyano group and a nitro group, or a phenyl-$C_1$–$C_4$ alkyl group wherein the phenyl moiety may optionally be substituted by one or two groups selected from a halogen atom, a $C_1$–$C_3$ alkyl group, a $C_1$–$C_3$ alkoxy group, a trifluoromethyl group, an amino group, a mono- or di-$C_1$–$C_3$ alkylamino group, a cyano group and a nitro group, or $R_1$ and $R_1$ may optionally combine together with the nitrogen atom to which they are attached to form a group of the formula:

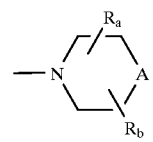

wherein A is a single bond, —$CH_2$—, —O— or —NH—, $R_a$ and $R_b$ are the same or different and each a hydrogen atom or a $C_1$–$C_6$ alkyl group, or when A is a single bond, and $R_a$ and $R_b$ are located at the 2-position and the 3-position, respectively, the carbon atoms of the 2-position and the 3-position and $R_a$ and $R_b$ may optionally combine to form a phenyl ring, $R_3$ is a hydrogen atom, a $C_1$–$C_6$ alkyl group or a hydroxy-$C_1$–$C_4$ alkyl group, $R_4$ is a hydrogen atom or a $C_1$–$C_6$ alkyl group, or $R_3$ and $R_4$ may optionally combine together with the carbon atom and the nitrogen atom to which they are attached to form pyrrolidine, piperidine, or 2,3-dihydro-1H-indole ring, $R_5$ is a hydrogen atom, a $C_1$–$C_6$ alkyl group; a $C_3$–$C_6$ alkenyl group; a hydroxy-$C_1$–$C_4$ alkyl group; a $C_1$–$C_4$ alkyl group substituted by a benzyloxy group wherein the phenyl moiety may optionally be substituted by one or two groups selected from a halogen atom, a $C_1$–$C_3$ alkyl group and a $C_1$–$C_3$ alkoxy group; a $C_1$–$C_4$ alkyl group substituted by a $C_2$–$C_4$ alkanoyloxy group or a benzoyloxy group which may optionally be substituted by one or two groups selected from a halogen atom, a $C_1$–$C_3$ alkyl group and a $C_1$–$C_3$-alkoxy group; a $C_1$–$C_5$ alkoxy-$C_1$–$C_4$ alkyl group; a trifluoromethyl group; a halogen atom; an amino group a mono or di-$C_1$–$C_4$ alkylamino group; a $C_2$–$C_4$ alkanoylamino group; a benzoylamino group which may optionally be substituted by one or two groups selected from a halogen atom, a $C_1$–$C_3$ alkyl group and a $C_1$–$C_3$ alkoxy group; an amino-$C_1$–$C_4$ alkyl group; a nitro group; a carbamoyl group; a mino- or di-$C_1$–$C_4$ alkylcarbamoyl group a carboxyl group; a carboxyl group being protected by a $C_1$–$C_4$ alkyl group or a benzyl group which may optionally be substituted by one or two groups selected from a halogen atom, a $C_1$–$C_3$ alkyl group and a $C_1$–$C_3$ alkoxy group; a carboxy-$C_1$–$C_4$ alkyl group; or a $C_1$–$C_4$ alkyl group being substituted by a carboxyl group which is protected by a $C_1$–$C_4$ alkyl group or a benzyl group which may optionally be substituted by one or two groups selected from a halogen atom, a $C_1$–$C_3$ alkyl group and a $C_1$–$C_3$ alkoxy group;

$R_6$ is a hydrogen atom, a $C_1$–$C_6$ alkyl group, a trifluoromethyl group or a phenyl group which may optionally be substituted by one or two groups selected from a halogen atom, a $C_1$–$C_3$ alkyl group, a $C_1$–$C_3$ alkoxy group, a trifluoro-methyl group, an amino group, a mono- or di-$C_1$–$C_3$ alkylamino group, a cyano group and a nitro group, or $R_5$ and $R_6$ may optionally combine to form —$(CH_2)_n$—, $R_7$ is a hydrogen atom, a halogen atom, a $C_1$–$C_6$ alkyl group, a $C_1$–$C_6$ alkoxy group, a trifluoromethyl group, a hydroxy group, an amino group, a mono- or di-$C_1$–$C_4$ alkylamino group, a cyano group or a nitro group, $R_8$ is a hydrogen atom, a halogen atom, a $C_1$–$C_6$ alkyl group or a $C_1$–$C_6$ alkoxy group, or a pharmaceutically acceptable acid addition salt thereof.

2. The compound according to claim 1, wherein $R_5$ is a hydrogen atom, a $C_1$–$C_6$ alkyl group, a hydroxy-$C_1$–$C_4$ alkyl group, a halogen atom, an amino group, a $C_2$–$C_4$ alkanoylamino group, a benzoylamino group which may optionally be substituted by one or two groups selected from a halogen atom, a $C_1$–$C_3$ alkyl group and a $C_1$–$C_3$ alkoxy group, a nitro group or a carboxyl group being protected by a $C_1$–$C_4$ alkyl group or a benzyl group which may optionally be substituted by one or two groups selected from a halogen atom, a $C_1$–$C_3$ alkyl group and a $C_1$–$C_3$ alkoxy group.

3. The compound according to claim 1, wherein $R_1$ and $R_2$ are the same or different and each a $C_1$–$C_6$ alkyl group, or $R_1$ is a $C_1$–$C_6$ alkyl group, a $C_3$–$C_6$ alkenyl group or a $C_3$–$C_8$ cycloalkyl-$C_1$–$C_4$ alkyl group, and $R_2$ is a phenyl group which may optionally be substituted by one or two groups selected from a halogen atom, a $C_1$–$C_3$ alkyl group, a $C_1$–$C_3$ alkoxy group, a trifluoromethyl group, an amino group, a mono- or di-$C_1$–$C_3$ alkylamino group, a cyano group and a nitro group, or $R_1$ and $R_2$ may optionally combine together with the nitrogen atom to which they are attached to form a group of the formula:

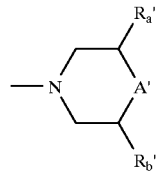

wherein A' is —$CH_2$— or —O—, and $R_a'$ and $R_b'$ are the same or different and each a $C_1$–$C_6$ alkyl group, and $R_5$ is a hydrogen atom, a $C_1$–$C_6$ alkyl group, a hydroxy-$C_1$–$C_4$ alkyl group, a halogen atom, an amino group, a $C_2$–$C_4$ alkanoylamino group, a benzoylamino group which may optionally be substituted by one or two groups selected from a halogen atom, a $C_1$–$C_3$ alkyl group and a $C_1$–$C_3$-alkoxy group, a nitro group or a carboxyl group being protected by a $C_1$–$C_4$ alkyl group or a benzyl group which may optionally be substituted by one or two groups selected from a halogen atom, a $C_1$–$C_3$ alkyl group and a $C_1$–$C_3$ alkoxy group.

4. The compound according to claim 1, wherein $R_1$ and $R_2$ are the same or different and each a methyl group, an ethyl group, a propyl group, an isopropyl group or a butyl group, or $R_1$ is a methyl group, an ethyl group, a propyl group, an isopropyl group, a butyl group, an allyl group or a cyclopropylmethyl group, and $R_2$ is a phenyl group or a phenyl group being substituted by a halogen atom or a methoxy group, $R_3$ is a hydrogen atom, $R_5$ is a hydrogen atom, a methyl group, an ethyl group or a hydroxymethyl group, $R_6$ is a methyl group or a phenyl group, or $R_5$ and $R_6$ may optionally combine to form —$(CH_2)_4$—, $R_7$ is a hydrogen atom, a halogen atom, a $C_1$–$C_3$ alkoxy group, a trifluoromethyl group, an amino group or a nitro group, and $R_8$ is a hydrogen atom.

5. The compound according to claim 4, wherein X is —O— or —$NR_4$—, $R_1$ and $R_2$ are the same or different and each an ethyl group, a propyl group or a butyl group, or $R_1$ is a methyl group, an ethyl group, a propyl group, an allyl group or a cyclopropylmethyl group, and $R_2$ is a phenyl group, a halogenophenyl group or a methoxyphenyl group, $R_3$ is a hydrogen atom, $R_4'$ is a hydrogen atom, a methyl group or an ethyl group, or $R_3$ and $R_4'$ may optionally combine together with the carbon atom and the nitrogen atom to which they are attached to form a pyrrolidine ring or a 2,3-dihydro-1H-indole ring, $R_7$ is a hydrogen atom, a halogen atom, a methoxy group, a trifluoromethyl group, an amino group or a nitro group, and $R_8$ is a hydrogen atom.

6. An acetamide derivative of the formula (I'):

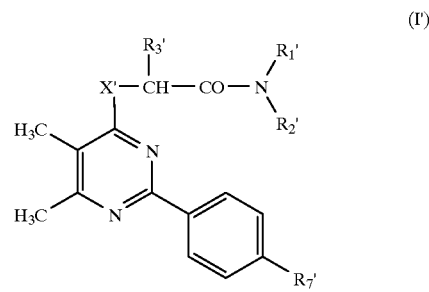

wherein X' is —O— or —$NR_4'$—, $R_1'$ and $R_2'$ are both an ethyl group or a propyl group, or $R_1'$ is a methyl group, an ethyl group, a propyl group, an allyl group or a cyclopropylmethyl group, $R_2'$ is a phenyl group or a 4-halogenophenyl group, or a 4-methoxyphenyl group, $R_3'$ is a hydrogen atom, $R_4''$ is a hydrogen atom, a methyl group, or an ethyl group, $R_7'$ is a hydrogen atom, a halogen atom, a methoxy group, a trifluoromethyl group, an amino group or a nitro group, or a pharmaceutically acceptable acid addition salt thereof.

7. The compound according to claim 6, wherein X' is —NH—.

8. The compound according to claim 6, wherein X' is —O—.

9. An acetamide derivative of the formula (I"):

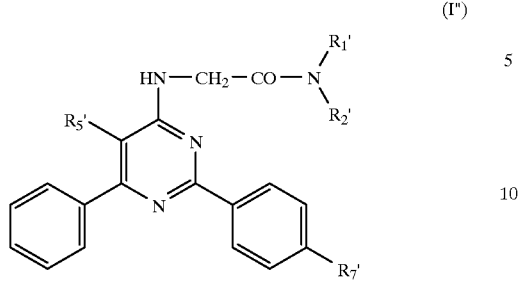

(I")

wherein $R_1'$ and $R_2'$ are both an ethyl group or a propyl group, or $R_1'$ is a methyl group, an ethyl group, a propyl group, an allyl group or a cyclopropylmethyl group, $R_2'$ is a phenyl group or a 4-halogenophenyl group or a 4-methoxyphenyl group, $R_5'$ is a hydrogen atom, a methyl group or an ethyl group, $R_7'$ is a hydrogen atom, a halogen atom, a methoxy group, a trifluoromethyl group, an amino group or a nitro group, or a pharmaceutically acceptable acid addition salt thereof.

10. A compound which is selected from the following compounds:

2-[2-(4-chlorophenyl)-5,6-dimethyl-4-pyrimidinyl amino]-N,N-diethyl-acetamide;

N-(4-chlorophenyl)-N-methyl-2-(5,6-dimethyl-2-phenyl-4-pyrimidinylamino)acetamide;

2-[2-(4-chlorophenyl)-5,6-dimethyl-4-pyrimidinylamino]-N-(4-fluorophenyl)-N-methylacetamide;

2-[2-(4-chlorophenyl)-5,6-dimethyl-4-pyrimidinylamino]-N-(4-methoxyphenyl)-N-methylacetamide;

2-(5,6-dimethyl-2-phenyl-4-pyrimidinylamino)-N-phenyl-N-propylacetamide: and

2-[2-(4-chlorophenyl)-5,6-dimethyl-4-pyrimidinylamino]-N-ethyl-N-phenylacetamide, or a pharmaceutically acceptable acid addition salt thereof.

11. A compound which is selected from the following compounds:

2-(5,6-dimethyl-2-phenyl,-4-pyrimidinyloxy)-N,N-dipropylacetamide;

2-(2,6-diphenyl-4-pyrimidinylamino)-N,N-dipropylacetamide;

2-[5,6-dimethyl-2-(4-trifluoromethylphenyl)-4-pyrimidinylamino]-N,N-dipropylacetamide;

N-ethyl-2-[5,6-dimethyl-2-(4-aminophenyl)-4-pyrimidinyloxy]-N-phenylacetamide;

2-[2-(4-chlorophenyl)-5,6-dimethyl-4-pyrimidinyloxy]-N-methyl-N-phenylacetamide; and 2-(5,6-dimethyl-2-phenyl-4-pyrimidinyloxy)-N-phenyl-N-propylacetamide, or a pharmaceutically acceptable acid addition salt thereof.

12. 2-[2-(4-Chlorophenyl)-5,6-dimethyl-4-pyrimidinylamino]-N,N-dipropylacetamide, or a pharmaceutically acceptable acid addition salt thereof.

13. 2-[2-(4-Chlorophenyl)-5,6-dimethyl-4-pyrimidinylamino]-N-methyl-N-phenylacetamide, or a pharmaceutically acceptable acid addition salt thereof.

14. A process for preparing an acetamide derivative of the formula (I):

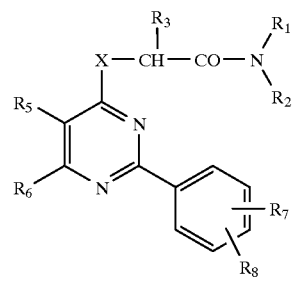

(I)

wherein X is —O— or —$NR_4$—, $R_1$ is a hydrogen atom, a $C_1$–$C_6$ alkyl group, a $C_3$–$C_6$ alkenyl group or a $C_3$–$C_8$ cycloalkyl-$C_1$–$C_4$ alkyl group, $R_2$ is a $C_1$–$C_6$ alkyl group, a $C_3$–$C_8$ cycloalkyl group, a phenyl group which may optionally be substituted by one or two groups selected from a halogen atom, a $C_1$–$C_3$ alkyl group, a $C_1$–$C_3$ alkoxy group, a trifluoromethyl group, an amino group, a mono- or di-$C_1$–$C_3$ alkylamino group, a cyano group and a nitro group, or a phenyl-$C_1$–$C_4$ alkyl group wherein the phenyl moiety may optionally be substituted by one or two groups selected from a halogen atom, a $C_1$–$C_3$ alkyl group, a $C_1$–$C_3$ alkoxy group, a trifluoromethyl group, an amino group, a mono- or di-$C_1$–$C_3$ alkylamino group, a cyano group and a nitro group, or $R_1$ and $R_2$ may optionally combine together with the nitrogen atom to which they are attached to form a group of the formula:

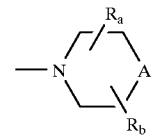

wherein A is a single bond, —$CH_2$—, —O— or —NH—, and $R_a$ and $R_b$ are the same or different and each a hydrogen atom or a $C_1$–$C_6$ alkyl group, or when A is a single bond, and $R_a$ and $R_b$ are located at the 2-position and the 3-position, respectively, the carbon atoms of the 2-position and the 3-position and $R_a$ and $R_b$ may optionally combine to form a phenyl ring, $R_3$ is a hydrogen atom, a $C_1$–$C_6$ alkyl group or a hydroxy-$C_1$–$C_4$ alkyl group, $R_4$ is a hydrogen atom or a $C_1$–$C_6$ alkyl group, or $R_3$ and $R_4$ may optionally combine together with the carbon atom and the nitrogen atom to which they are attached to form a pyrrolidine, a piperidine, or a 2,3-dihydro-1H-indole ring, $R_5$ is a hydrogen atom; a $C_1$–$C_6$ alkyl group; a $C_3$–$C_6$ alkenyl group; a hydroxy-$C_1$–$C_4$ alkyl group, a $C_1$–$C_4$ alkyl group substituted by a benzyloxy group wherein the phenyl moiety may optionally be substituted by one or two groups selected from a halogen atom, a $C_1$–$C_3$ alkyl group and a $C_1$–$C_3$ alkoxy group; a $C_1$–$C_4$ alkyl group substituted by a $C_2$–$C_4$ alkanoyloxy group or a benzoyloxy group which may optionally be substituted by one or two groups selected from a halogen atom, a $C_1$–$C_3$ alkyl group and a $C_1$–$C_3$-alkoxy group; a $C_1$–$C_6$ alkoxy-$C_1$–$C_4$ alkyl group; a trifluoromethyl group, a halogen atom; an amino group; a mono- or di-$C_1$–$C_4$ alkylamino group; a $C_2$–$C_4$ alkanoylamino group; a benzoylamino group which may optionally be substituted by one or two groups selected from a halogen atom, a $C_1$–$C_3$ alkyl group and a $C_1$–$C_3$ alkoxy group; an amino-$C_1$–$C_4$ alkyl group; a nitro group; a carbamoyl group; a mono- or di-$C_1$–$C_4$ alkylcarbamoyl group; a carboxyl group; a carboxyl group being protected by a $C_1$–$C_4$ alkyl group or a benzyl group which may optionally be substituted by one or two groups selected from a halogen atom, a $C_1$–$C_3$ alkyl group and a $C_1$–$C_3$ alkoxy group; a carboxy-$C_1$–$C_4$ alkyl group; or a $C_1$–$C_4$ alkyl group being substituted by a carboxyl group which is protected by a $C_1$–$C_4$ alkyl group or a benzyl group which may optionally be substituted by one or two groups selected from a halogen atom, a $C_1$–$C_3$ alkyl group and a $C_1$–$C_3$ alkoxy group;

$R_6$ is a hydrogen atom, a $C_1$–$C_6$ alkyl group, a trifluoromethyl group or a phenyl group which may optionally be substituted by one or two groups selected from a halogen atom, a $C_1$–$C_3$ alkyl group, a $C_1$–$C_3$ alkoxy group a trifluoro-methyl group an amino group, a mono- or di-$C_1$–$C_3$ alkylamino group, a cyano group and a nitro group, or $R_5$ and $R_6$ may optionally combine to form —$(CH_2)_n$—, $R_7$ is a hydrogen atom, a halogen atom, a $C_1$–$C_6$ alkyl group, a $C_1$–$C_6$ alkoxy group, a trifluoromethyl group, a hydroxy group, an amino group, a mono- or di-$C_1$–$C_4$ alkylamino group, a cyano group or a nitro group, $R_8$ is a hydrogen atom, a halogen atom, a $C_1$–$C_6$ alkyl group or a $C_1$–$C_6$ alkoxy group, or a pharmaceutically acceptable acid addition salt thereof, which comprises the following processes (a), (b), (c), (d), or (e):

(a): when the compound (I) is a compound of the formula (I) wherein X is —$NR_4$— reacting a compound of the formula (II):

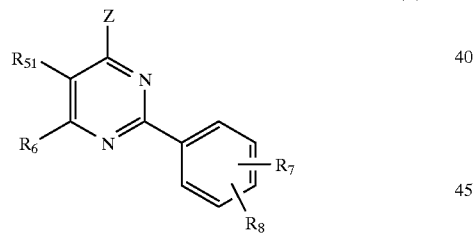

(II)

wherein Z is a leaving atom or a leaving group, $R_{51}$ is the same groups as defined above for $R_5$ except that a hydroxy-$C_1$–$C_4$ alkyl group, an amino group, an amino-$C_1$–$C_4$ alkyl group, a carboxyl group and a carboxy-$C_1$–$C_4$ alkyl group are protected ones, and $R_6$, $R_7$ and $R_8$ are the same as defined above, with a compound of the formula (III):

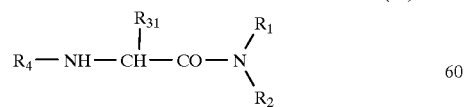

(III)

wherein $R_{31}$ is a hydrogen atom, a $C_1$–$C_6$ alkyl group or a hydroxy-$C_1$–$C_4$ alkyl group being protected by a benzyloxy group, a 4-chlorobenzyloxy group, a 3-bromobenzyloxy group, a 4-fluoribenzyloxl group, a 4-methylbenzyloxy group, or a 4-methoxybenzyloxy group, and $R_1$, $R_2$ and $R_4$ are the same as defined above, optionally followed by removing the protecting groups from the product, or (b) when the compound (I) is a compound of the formula (I) wherein X is —O—, and $R_3$ is a hydrogen atom, reacting a compound of the formula (II):

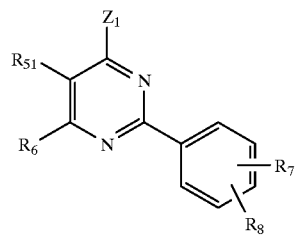

(II')

wherein $Z_1$ is a halogen atom, and $R_{51}$, $R_6$, $R_7$ and $R_8$ are the same as defined above, with a compound of the formula (V):

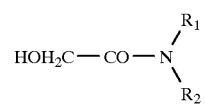

(V)

wherein $R_1$ and $R_2$ are the same as defined above in the presence of a base, and optionally followed by removing the protecting groups from the product, or (c) when the compound (I) is a compound of the formula (I) wherein X is —O—, reacting a compound of the formula (IVa):

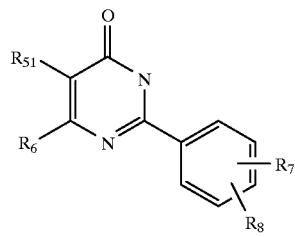

(IVa)

wherein $R_{51}$, $R_6$, $R_7$ and $R_8$ are the same as defined above, with a compound of the formula (VII):

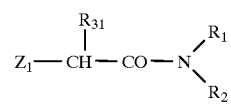

(VII)

wherein $Z_1$, $R_1$, $R_2$ and $R_{31}$ are the same as defined above in the presence of a base, if necessary, followed by removing the protecting groups from the product, or (d) reacting a compound of the formula (VIII):

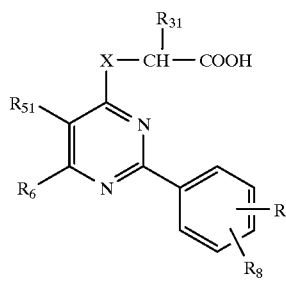

(VIII)

wherein X, $R_{31}$, $R_{51}$, $R_6$, $R_7$ and $R_8$ are the same as defined above, or a reactive derivative thereof, with a compound of the formula (IX):

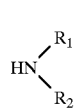

(IX)

wherein $R_1$ and $R_2$ are the same as defined above, optionally followed by removing the protecting groups from the product, or (e) when the compound (I) is a compound of the formula (I) wherein $R_1$ is a $C_1$–$C_6$ alkyl group, a $C_3$–$C_6$ alkenyl group or a $C_3$–$C_8$ cycloalkyl-$C_{1-C4}$ alkyl group, reacting a compound of the formula (XII):

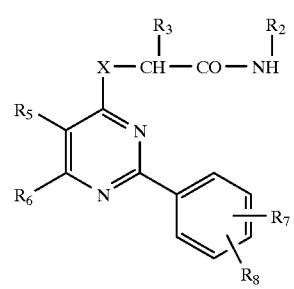

(XII)

wherein X, $R_2$, $R_3$, $R_5$, $R_6$, $R_7$, and $R_8$ are the same as defined above, with a compound of the formula (XIII):

$R_{11}$—$Z_1$ wherein $R_{11}$ is a $C_1$–$C_6$ alkyl group, a $C_3$–$C_6$ alkenyl group or a $C_3$–$C_8$ cycloalkyl-$C_{1-C4}$ alkyl group, and $Z_1$ is the same as defined above in a solvent, optionally followed by removing any protecting groups from the product, and optionally converting the product thus obtained into a pharmaceutically acceptable acid addition salt thereof.

15. A pharmaceutical composition which contains as an active ingredient a therapeutically effective amount of the acetamide derivative as set forth in claim 1, or a pharmaceutically acceptable acid addition salt thereof, and a pharmaceutically acceptable carrier or diluent.

16. A pharmaceutical composition which contains as an active ingredient a therapeutically effective amount of the acetamide derivative as set forth in claim 6, or a pharmaceutically acceptable acid addition salt thereof, and a pharmaceutically acceptable carrier or diluent.

17. A method for treatment of neurosis, somatoform disorders and anxiety disorders, which comprises administering a therapeutically effective amount of the acetamide derivative as set forth in claim 1, or a pharmaceutically acceptable acid addition salt thereof, to a patient with neurosis, somatoform disorders and anxiety disorders.

18. A method for treatment of immuno inflammatory diseases, which comprises administering a therapeutically effective amount of the acetamide derivative as set forth in claim 1, or a pharmaceutically acceptable acid addition salt thereof, to a patient with immuno inflammatory diseases.

19. A method for treatment of immuno inflammatory diseases, which comprises administering a therapeutically effective amount of one of the following compounds:

2-(5,6-dimethyl-2-phenyl-4-pyrimidinyloxy)-N,N-dipropyl-acetamide;

2-(2,6-diphenyl-4-pyrimidinylamino)-N,N-dipropylacetamide;

2-[5,6-dimethyl-2-(4-trifluoromethylphenyl)-4-pyrimidinyl-amino]-N,N-dipropylacetamide;

2-[2-(4-aminophenyl)-5,6-dimethyl-4-pyrimidinyloxy]-N-ethyl-N-phenylacetamide;

2-[2-(4-chlorophenyl)-5,6-dimethyl-4-pyrimidinyloxy]-N-methyl-N-phenylacetamide; and 2-(5,6-dimethyl-2-phenyl-4-pyrimidinyloxy)-N-phenyl-N-propyl-acetamide, or a pharmaceutically acceptable acid addition salt thereof, to a patient of immuno inflammatory disease.

* * * * *